(12) United States Patent
Boucher et al.

(10) Patent No.: US 11,011,271 B2
(45) Date of Patent: May 18, 2021

(54) DEVICES, METHODS AND SYSTEMS FOR ACQUIRING MEDICAL DIAGNOSTIC INFORMATION AND PROVISION OF TELEHEALTH SERVICES

(71) Applicant: Zipline Health, Inc., San Francisco, CA (US)

(72) Inventors: Ryan Boucher, San Francisco, CA (US); Lionel Nelson, Los Altos Hills, CA (US)

(73) Assignee: Zipline Health, Inc., San Francisco, CA (US)

( * ) Notice: Subject to any disclaimer, the term of this patent is extended or adjusted under 35 U.S.C. 154(b) by 0 days.

(21) Appl. No.: 15/920,208

(22) Filed: Mar. 13, 2018

(65) Prior Publication Data

US 2018/0360295 A1 Dec. 20, 2018

Related U.S. Application Data

(63) Continuation of application No. 13/929,591, filed on Jun. 27, 2013, now abandoned.
(Continued)

(51) Int. Cl.
*G16H 40/67* (2018.01)
*A61B 1/227* (2006.01)
(Continued)

(52) U.S. Cl.
CPC ......... *G16H 40/67* (2018.01); *A61B 1/00016* (2013.01); *A61B 1/00179* (2013.01);
(Continued)

(58) Field of Classification Search
CPC ....... A61B 1/00016; A61B 1/24; A61B 1/227; A61B 1/00179; A61B 1/00181;
(Continued)

(56) References Cited

U.S. PATENT DOCUMENTS

| 5,489,256 A | * | 2/1996 | Adair | ................. | A61B 1/00073 |
| | | | | | 600/123 |
| 5,658,235 A | | 8/1997 | Priest et al. |

(Continued)

FOREIGN PATENT DOCUMENTS

| JP | H10-258023 A | 9/1998 |
| JP | H11-113841 A | 4/1999 |

(Continued)

OTHER PUBLICATIONS

PCT International Preliminary Report on Patentability, PCT Application No. PCT/US2013/048316, dated Dec. 31, 2014, six pages.
(Continued)

*Primary Examiner* — Aaron B Fairchild
(74) *Attorney, Agent, or Firm* — Fenwick & West LLP

(57) ABSTRACT

The invention relates generally to various systems, tools and methods for acquiring diagnostic information, including medical information, for a user, transmitting the information to a remote location, assessing the information, and transmitting resulting diagnosis and treatment information to the user and/or a third party for subsequent action. The present invention provides consumer and user-friendly telemedicine systems and procedures which enable health services and/or diagnosis to be provided at a distance remotely.

11 Claims, 17 Drawing Sheets

Related U.S. Application Data

(60) Provisional application No. 61/664,920, filed on Jun. 27, 2012.

(51) Int. Cl.

| | | |
|---|---|---|
| *A61B 1/24* | (2006.01) | |
| *A61B 1/00* | (2006.01) | |
| *A61B 1/04* | (2006.01) | |
| *A61B 7/04* | (2006.01) | |
| *G16H 30/20* | (2018.01) | |
| *H04W 4/90* | (2018.01) | |
| *A61B 5/00* | (2006.01) | |
| *G16H 10/60* | (2018.01) | |

(52) U.S. Cl.
CPC ............ *A61B 1/00181* (2013.01); *A61B 1/04* (2013.01); *A61B 1/227* (2013.01); *A61B 1/24* (2013.01); *A61B 7/04* (2013.01); *G16H 30/20* (2018.01); *A61B 5/0022* (2013.01); *A61B 5/7282* (2013.01); *G16H 10/60* (2018.01); *H04W 4/90* (2018.02)

(58) Field of Classification Search
CPC ... A61B 1/0051; A61B 1/0052; A61B 1/0053; A61B 1/0055; A61B 1/0056; A61B 1/0057; A61B 1/0058; A61B 1/008; A61B 1/00082; A61B 1/233
USPC .......................................................... 600/146
See application file for complete search history.

(56) References Cited

U.S. PATENT DOCUMENTS

| | | | |
|---|---|---|---|
| 5,701,904 A | 12/1997 | Simmons et al. | |
| 6,319,199 B1 | 11/2001 | Sheehan et al. | |
| 7,025,061 B2 | 4/2006 | Haussmann | |
| 2002/0022763 A1* | 2/2002 | Sano .................. | A61B 1/00016 600/109 |
| 2002/0038076 A1 | 3/2002 | Sheehan et al. | |
| 2002/0118279 A1* | 8/2002 | Spoonhower ............ | A61B 1/24 348/66 |
| 2003/0016284 A1 | 1/2003 | Squilla et al. | |
| 2003/0100819 A1 | 5/2003 | Newman et al. | |
| 2004/0073455 A1 | 4/2004 | McConnochie et al. | |
| 2004/0249246 A1* | 12/2004 | Campos .................. | A61B 1/307 600/160 |
| 2005/0038317 A1* | 2/2005 | Ratnakar ............ | A61B 1/00105 600/101 |
| 2005/0272975 A1* | 12/2005 | McWeeney ....... | A61M 25/0068 600/113 |
| 2006/0149129 A1* | 7/2006 | Watts .................. | A61B 1/0676 600/113 |
| 2009/0198111 A1 | 8/2009 | Nearman et al. | |
| 2009/0203986 A1 | 8/2009 | Winnick | |
| 2010/0249513 A1 | 9/2010 | Tydlaska | |
| 2010/0261968 A1 | 10/2010 | Nearman et al. | |
| 2010/0305409 A1 | 12/2010 | Chang | |
| 2011/0224493 A1* | 9/2011 | Oyadiran ............. | A61B 5/0084 600/200 |
| 2011/0257481 A1* | 10/2011 | Ogawa ............... | G02B 23/2484 600/109 |

FOREIGN PATENT DOCUMENTS

| | | |
|---|---|---|
| JP | 2002-132958 A | 5/2002 |
| JP | 2007-500541 A | 1/2007 |
| KR | 2002-0009302 A | 2/2002 |
| WO | WO 02/056756 A2 | 7/2002 |
| WO | WO 2012/058641 A2 | 5/2012 |
| WO | WO 2014/004905 A1 | 1/2014 |

OTHER PUBLICATIONS

PCT International Search Report, PCT Application No. PCT/US2013/048316, dated Oct. 24, 2013, three pages.
PCT Written Opinion, PCT Application No. PCT/US2013/048316, dated Oct. 24, 2013, six pages.
Canadian Intellectual Property Office, Office Action, CA Patent Application No. 2,877,717, dated Apr. 5, 2018, five pages.
European Patent Office, Extended European Search Report and Opinion, EP Patent Application No. 13808431.4, dated Oct. 7, 2016, 14 pages.
United States Office Action, U.S. Appl. No. 13/929,591, dated Jul. 18, 2017, 23 pages.
Japan Patent Office, Office Action, JP Patent Application No. 2018-072800, dated Jul. 2, 2019.
European Patent Office, Extended European Search Report and Opinion, EP Patent Application No. 20179958.2, dated Jan. 22, 2021, 13 pages.

\* cited by examiner

EXAMPLES OF USER SYSTEMS AND DEVICES (3 different examples)

Horizontal Section, LT Ear, View of Superior Half – from Gray's Anatomy

Trace of Above Section - Key Anatomy

EAR IMAGING AND DEVICES:

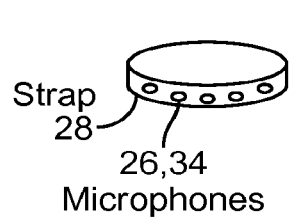
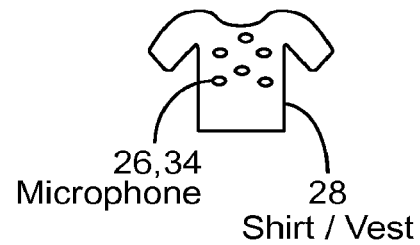
FIG. 32　　　　　FIG. 33
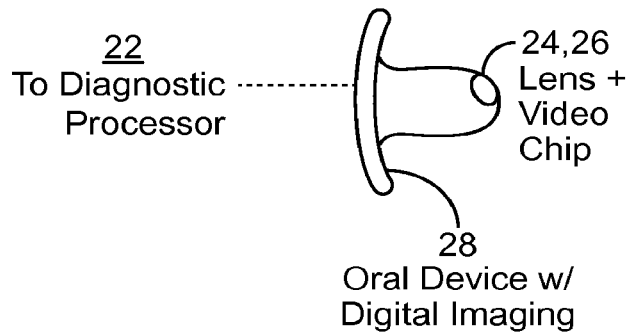
FIG. 34
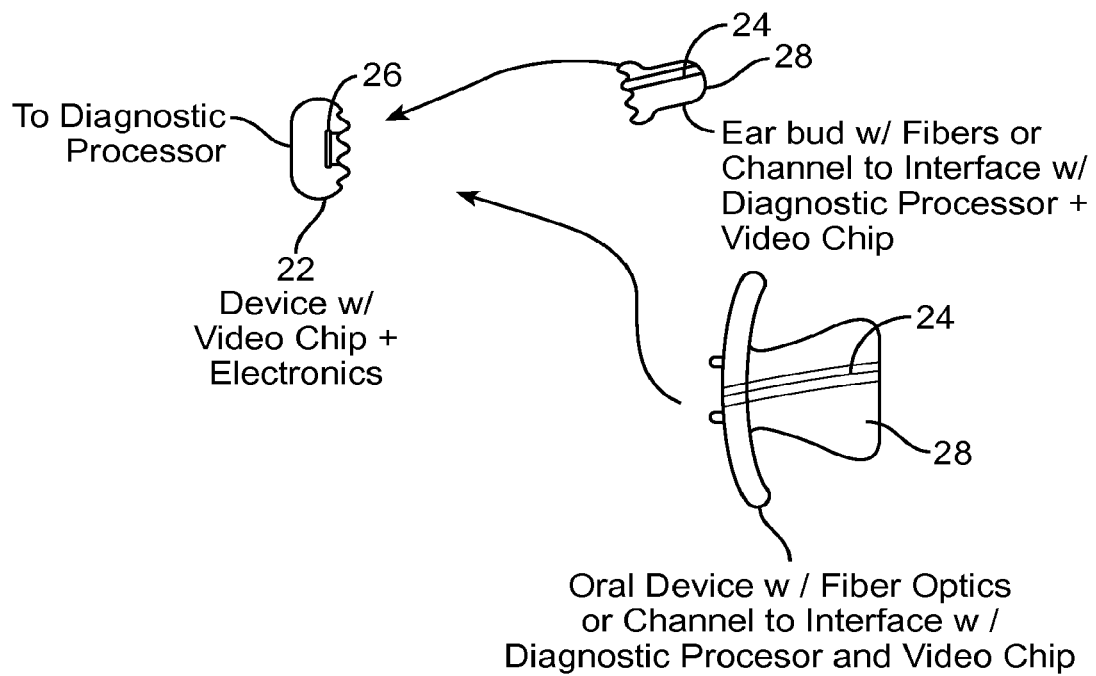
FIG. 35

DEVICES, METHODS AND SYSTEMS FOR ACQUIRING MEDICAL DIAGNOSTIC INFORMATION AND PROVISION OF TELEHEALTH SERVICES

RELATED APPLICATIONS

This application is a continuation of U.S. application Ser. No. 13/929,591, filed Jun. 27, 2013 (now abandoned), which claims the priority benefit of U.S. provisional patent application Ser. No. 61/664,920, filed on Jun. 27, 2012. The specifications of each of the foregoing applications are incorporated herein by reference in their entirety.

FIELD OF THE INVENTION

The invention relates generally to various systems, tools and methods for acquiring diagnostic information, including medical information, for a user, transmitting the information to a remote location, assessing the information, and transmitting resulting diagnosis and treatment information to the user and/or a third party for subsequent action. More specifically, the present invention relates to consumer and user-friendly telemedicine systems and procedures which enable health services and/or diagnoses to be provided remotely.

BACKGROUND OF THE INVENTION

Currently, patients with an injury or undiagnosed pain are typically forced to visit one or more physicians or medical treatment centers to have their condition diagnosed. If the patient is a small child, or if the condition is thought to be serious or in need of immediate treatment, the long waiting periods for a physician appointment may seem unreasonable or unacceptable, and the patient often ends up going to an emergency room and/or urgent care center on a "walk-in" basis. At the medical facility, the patient (or his/her guardian or caregiver) fills out medical history forms, answers questions about the condition, and has a clinician perform a physical examination to learn about the condition. In many cases, the waiting period at the facility can consume many hours, depending upon facility capacity and other patient needs (e.g., emergency cases treated as priority, etc.). Ultimately, the patient's visit may have been unnecessary, as the condition was not truly "urgent" or "critical," and thus treatment could have been delayed and/or accommodated at a regularly scheduled appointment, or the condition would have resolved itself with little or no intervention by the physician.

In many cases, the stress and uncertainty associated with the patient's condition can be more debilitating than the condition itself, especially where the patient is a small child, and the caregiver is an inexperienced parent who is anxious about his or her child's condition. Moreover, because emergency treatment centers such as emergency rooms and urgent care centers are operating at or over capacity, the long wait times at such facilities can further exacerbate stress, leading to a wide variety of potential medical situations including hypertension, heart attacks and/or strokes, as well as possible physical and/or mental altercations between patients and/or caregivers. Moreover, the unnecessary use of emergency and urgent care facilities levies a heavy cost on the nation's health care and health care insurance systems, as such services are generally much more expensive than similar services provided on a scheduled or appointed basis.

SUMMARY OF THE INVENTION

The various inventions disclosed herein include the identification of a need for consumer- and/or user-friendly devices that can be employed by untrained or semi-trained individuals to safely and effectively capture, store, transmit, display, download and/or update medical or other information, including assessments, examinations, and evaluations of a patient's condition via electronic media for use by patients, clinicians, health care providers, and system administrators. In accordance with one exemplary embodiment of the present disclosure, the method includes, without limitation, a non-medical professional (e.g., a consumer or other patient, etc.) utilizing a device to perform an examination protocol for a patient's condition, the device having the capability to store and/or transmit relevant information for use in an asynchronous or other telemedicine environment. The performing of the examination can include storing information about the patient's condition in a storage medium, include storage media accessed remotely (e.g., USB accessible, LAN accessible and/or internet accessible storage devices), as well as localized storage associated with the device (e.g., RAM or flash memory, SD cards, attached smartphone memory, etc.). The device can simultaneously and/or subsequently upload stored data to a general or specialized storage network, or remote access to the electronic storage medium can be provided over a computer or other communication network. The stored data can then be accessed by a competent medical professional or other caregiver, properly assessed, and recommendations regarding the condition and/or treatment can be transmitted or otherwise given to the patient or guardian.

Various embodiments disclosed herein include the manufacture, distribution and use of specialized and/or generalized devices that can be utilized by non-medical personnel (e.g., consumers) to collect patient information in a home-care or non-medical facility location. The information can then be transmitted and/or otherwise accessed by qualified medical and care-giving personnel, and appropriate assessment, condition and/or treatment information can be transmitted or otherwise provided to the patient. In various embodiments, the device can be a part of and/or used in conjunction with electronic communications and/or display systems such as telephones, cell phones, smart phones, computers, wireless radios and/or other communications media known in the art. Desirably, the disclosed systems will allow a patient to transmit sufficient information to the medical professional to enable assessment of the patient's condition, which may include information relevant to immediate and/or critical treatment of the condition that may not be readily apparent to the patient. In various embodiments, the inventive systems allow trained personnel to direct the patient's actions and/or use of the diagnostic tools, such as requesting information regarding specific anatomical features which may be imaged by the diagnostic device in the hands of the patient as requested "real time" by the physician.

In various embodiments, the disclosed systems and methods include the ability to collect patient information at a plurality of times or conditions, whereby the information can be transmitted and/or otherwise accessed by the medical professional and used in the assessment of the patient's condition. Such information may be stored for various periods of time, at differing locations, and previously-stored data can be transmitted and/or made available in conjunction with current patient information and used in the assessment of the patient's condition. Similarly, patient information collected via other methods, including routine physicals and/or during doctor office visits, can be collected and provided with current patient information in a similar manner. If desired, the specialized and/or generalized consumer device (or other device such as a smartphone or computer) can include memory features that collect and store such information, such as the identity and dosages of medicines currently being taken by the patient or the fact that the patient has diabetes or other medical conditions.

Various alternative embodiments include the provision of an internet-accessible healthcare system to consumers, whereby the consumer can provide patient information (as previously described) to the system, and can receive assessment, condition and/or treatment information from a healthcare professional associated with the system. In various embodiments, the system can provide the consumer and/or patient with status updates and/or other relevant information during the process to: (1) confirm receipt and/or integrity of the relevant patient information, including patient medical data and payment information, if necessary, (2) identify various steps of the process, and the patient information's current status (e.g., data assigned to a physician or specialist, data currently being reviewed, medical recommendations being prepared, system scheduling a local physician visit on patient's behalf, system directing patient to a local emergency room, system dispatches an ambulance or paramedics to the patient's location, etc.), (3) request additional information from the patient (either using the current device and/or additional devices, some of which may be immediately available to the patient) which may include initiating a live-call or other communication between the medical professional and the patient, (4) providing assessment, treatment and/or other information to the patient, and (5) forwarding prescription or other treatment information to the patient, hospital, pharmacy or other care-giver as requested by the patient and/or assigned by the system. In various embodiments, the provision of the type of updates can significantly reduce patient anxiety while waiting for treatment information, as well as confirm to the patient whether the patient information has been received and/or is being reviewed by the system. In addition, in situations where the patient is unable or unwilling to access emergency services directly (e.g., the patient is stuck in an accident on the road, lost in the wildness, climbing a mountain, located in a collapsed building, etc.), the present system and methods described herein can provide critical care data directly to the patient, as well as provide emergency response personnel with detailed information about a patient's condition, that may take mere seconds for the device to collect, allowing responders to prioritize their response and/or equip themselves for specialized medical responses.

In various embodiments, the present system can be associated with various healthcare-providing organizations and/or payors, including clinics, hospitals, insurance companies, employers and/or governmental entities, as necessary and/or allowed by current or future laws (e.g., privacy and health care information accessibility statutes, etc). The use of such systems by such entities can significantly reduce congestion of existing emergency as well as non-emergency health services (by reducing the number and/or frequency of unnecessary patient visits) as well as significantly improve the provision of health care to the general consuming population in a highly effective and cost-efficient manner. Moreover, various embodiments of the system can significantly reduce the need for medical professionals to be located proximate to their patients, and can even promote and/or encourage "time shifting" of medical care by patients and/or medical professionals.

Various technical features of the invention generally relate to devices, systems and methods that facilitate remote connection and communication between two or more parties for medical, health and/or wellness purposes, herein collectively referred to as telehealth. In various embodiments, technical features are disclosed that generally relate to devices, systems and methods for capturing, displaying, recording and/or transmitting diagnostic information, including remote control manipulation of devices and/or diagnostic information. Other technical features of the invention generally relate to devices, systems and methods that provide the infrastructure, logistics and user interfaces to make possible remote or at home diagnosis, advice and/or coaching for medical, health and/or wellness purposes (herein collectively referred to as health purposes). Other technical features of the invention generally relate to devices, systems and methods providing advanced features for a more pleasurable user experience and/or more elaborate telehealth system.

In various embodiments, the systems and methods disclosed herein can facilitate one or more of the following (including various combinations thereof):

A. Reduction of health care costs for both payer and patient/consumer;

B. Providing adequate patient access to primary care physicians. The invention desirably accommodates reducing the number of primary care physicians and increasing the number of patients able to be served;

C. Early diagnosis focusing to help minimize disease progression;

D. Accommodation of modern fast-paced life/culture. Modern communications methods and widespread internet/wireless connections have created consumers' expectations for more convenient and more rapid answers and access to information, including 24-hour and/or "real time" access to services;

E. Consumer-friendly and/or ruggedized information capture devices: The invention provides access to telemedicine and creates a need for the ability to capture diagnostic information remotely; and F. Reduction of the number of high-cost visits to an emergency room or facility/urgent care.

In various alternative embodiments, similar systems and methods as described herein could have varying levels of utility in non-health care applications, including the collection of relevant data using similar devices and/or the provision of "expert" advice for various other purposes, including non-medical diagnostics such as carpentry, plumbing, auto repair, etc.

It is to be understood that a reference to an individual encompasses singular and plural instances of the individual. For example, a medical care professional or provider may be a single person providing medical care, or multiple individuals working in concert to provide complementary service(s) to the patient or caregiver. Similarly, a caregiver can be a single individual such as a parent, or multiple individuals such as attendants at a nursing home.

In certain instances herein, components of the invention may alternatively be referred to as elements. These terms, as well as other comparable terms, are to be considered as interchangeable.

An embodiment of one aspect of the present invention is directed to an imaging apparatus for obtaining images inside a patient's ear canal. The imaging apparatus according to this embodiment comprises a main body and an extension having a central axis structurally configured for insertion into the patient's ear canal. The imaging apparatus comprises an imaging element for obtaining images which are angled and/or offset relative to the central axis of the extension into the ear canal. Alternatively, the imaging apparatus may be configured to obtain images in line with the central axis of the extension but where the extension is offset and/or angled relative to the ear canal central axis. Further, the imaging apparatus may obtain images which are angled and/or offset relative to the central axis of the extension and angled and/or offset relative to the central axis of the ear canal. The main body and/or extension may engage with the outer ear or ear canal to encourage these positions The imaging apparatus may comprise an engagement member which is structurally configured to be supported in-use by a patient's ear or head so that the user, provider, or caregiver does not need to support or hold the apparatus in position.

The imaging apparatus may comprise a wireless transmission element for wirelessly transmitting the obtained images to a processing or computing device. Alternatively, the imaging apparatus may communicate with a processing or computing device via a wired connection. A non-limiting list of examples of computing devices include mobile telephones, smartphones, laptop computers, tablet computers, desktop computers, servers, mainframes, and dedicated hardware computing devices. These devices can operate using mobile operating systems such as iOS (from Apple Inc.) and Android (from Google Inc.), desktop operating systems such as OSX (from Apple Inc.) and Windows (from Microsoft Corp.), or any other kind of operating system or platform. The computing device can also be custom-designed and manufactured for use specifically with the imaging apparatus.

The extension portion of the imaging apparatus may have a soft outer surface for improved patient comfort during insertion of the extension into the patient's ear canal.

An embodiment of another aspect of the present invention is directed to an oral imaging apparatus in the shape of a pacifier. The imaging apparatus may comprise an imaging element configured for taking an image of the oral cavity of a patient; and a transmission element for transmitting the image to a processing or computing device.

An embodiment of another aspect of the present invention is directed to a kit for collecting diagnostic information of a patient. Although different embodiments of the kit may contain different components, a useful combination comprises a main body and one or more attachments. The main body comprises diagnostic equipment, such as processing and/or computing elements, for obtaining medical diagnostic information of the patient, and a transmission element for transmitting the diagnostic information via wired or wireless connection to a computing device.

A useful first attachment for the main body comprises an imaging element structurally configured for imaging the ear canal and/or the ear drum of the patient. A useful second attachment for the main body comprises an imaging element structurally configured for imaging the oral cavity and/or throat of the patient. The kit may also comprise a third attachment having a sound accessing element structurally configured to obtain internal sounds of the patient's body. The kit may comprise any combination of first and/or second and/or third attachments.

The transmission element in the kit may be configured to transmit the diagnostic information in real time as the device is in use, or the diagnostic information may be transmitted upon receipt of an instruction from a user or provider. The transmission element may have the capability of transmitting the diagnostic information in a plurality of image resolutions, image sizes, or transmission speeds, or combinations thereof. For example, the transmission element can be configured to send images at VGA, SVGA, HVGA, or another resolution, or video at 12 frames per second, 24 frames per second, or another frame rate.

Any of the components of the kit such as the main body may be structurally configured as a hands-free unit while in-use, or as a handheld unit while in-use.

Another aspect of the present invention provides for a method of remotely providing medical information to a patient by a health care professional. The method may comprise the steps of:

a. providing, via a remote connection, the patient's current medical data to the health care professional;

b. optionally providing the health care professional with the patient's medical history;

c. causing the health care profession to develop an assessment of the patient's current physical condition on the basis of the current medical data and the medical history if available; and d. communicating the assessment to the patient or patient's caregiver over an electronic communications channel.

The method may also include providing, by the health care professional, the patient or patient's caregiver with treatment information. The treatment instructions can include any kind of medical advice or instructions, such as providing the patient with a prescription for a drug or a laboratory procedure; directions to visit a medical care provider, pharmacy, hospital, or laboratory. Multiple instructions can also be given to multiple parties. For example, the health care professional can provide (a) the patient's caregiver with verbal medical care instructions; (b) a pharmacy with a prescription for filling; and (c) a laboratory with advance notice that the patient will need a certain kind of test to be performed.

Another aspect of the present invention is directed to a method of remotely providing medical information by a health care provider to a patient. The method may comprise the steps of:

a. providing, via a remote connection, instructions to an untrained or semi-trained consumer to perform an examination protocol for a patient's condition using an examination device which stores and/or transmits current patient medical data for use in an asynchronous or telemedicine environment;

b. transmitting, by the consumer, the examination protocol data to the health care provider;

c. causing the healthcare provider to develop an assessment of the patient's current physical condition on the basis of the data obtained by the examination device; and d. communicating the assessment to the patient or the patient's caregiver over the remote connection.

The method may further comprise providing, by the health care professional, the patient or patient's caregiver with treatment information for the patient.

The examination protocol data can be transmitted to the health care provider in real time, as the data is acquired, or not in real time, for example, upon receipt of an instruction or request from the provider or health care professional for this data. In such embodiments, the examination protocol data can be stored in a storage medium such as a flash drive in a device participating in the performance of the invention.

An embodiment of another aspect of the present invention is directed to an examination device for performing an examination protocol for a patient's condition. The examination device can comprise:

a. an anatomical interface structurally configured for application to a predetermined area of the patient's body;

b. an accessing and capturing component which obtains current medical data of the patient after application of the anatomical interface to the patient's body;

c. a diagnostic processing component which processes the medical data obtained by the accessing and capturing component; and d. a communications link over which the processed medical data is transmitted to a communications component for viewing and interpretation by a medical care provider.

The anatomical interface is structurally configured for application to the patient's ear, nose, throat, eye, wrist, skin, head, skin, extremities, torso, or into a body orifice such as the inside of the mouth or nose. In this manner, the anatomical interface of the device will facilitate providing accurate patient medical status information.

Any of the disclosed devices, systems, or components may comprises a remote control component which is structurally configured to respond to control signals sent remotely by the medical care provider or a caregiver over a communications link. The communications link can transmit the obtained medical data in the form of still images, a video feed, an audio feed, a data stream, or a combination thereof, to the medical care provider.

Any of the disclosed devices, systems, or components may comprises a port or jack configured for attachment to a computing device such as a mobile telephone, laptop computer, tablet computer, or desktop computer. The port or jack may be conventional such as a minijack, USB port, Apple iDevice port (such as an iPhone or iPad), or custom-designed by the manufacturer.

Examples of the accessing and capturing component of the present invention include a mobile telephone, laptop computer, tablet computer, desktop computer, or a custom-designed hardware element.

Examples of the diagnostic processing component of the present invention include a mobile telephone, laptop computer, tablet computer, desktop computer, or a custom-designed hardware element. In certain embodiments of the invention, the accessing and capturing component and the diagnostic processing component can be the same hardware element. That is, the hardware element can have multiple functions as discussed and provided in this specification.

An embodiment of another aspect of the present invention is directed to a telehealth system for remote diagnosis of a patient's medical condition. The telehealth system can comprise elements such as:

A. a user subsystem configured for receiving a patient's current medical data, the user subsystem comprising:
 1. a communication device;
 2. a diagnostic processing device; and
 3. a diagnostic capture device;

B. a provider subsystem configured for communicating with a health care provider, the provider subsystem comprising:
 1. a communication device; and C. an infrastructure subsystem configured to process and store medical data and diagnostic information received from the user subsystem and the provider subsystem, the instrastructure subsystem comprising:
 1. an application server comprising computer instruction code configured to communication with:
  a. a database configured to store a patient's personal information and electronic health record;
  b. diagnostic computer instruction code configured to receive current patient medical information and to provide diagnostic information concerning the patient's medical condition; and
  c. a database configured to store archived diagnostic information;
 2. a server comprising computer instruction code configured to communicate with one or more third-party patient personal information or electronic health record databases; and
 3. a server comprising computer instruction code configured to communicate with a third party telehealth system, wherein the user, provider, and infrastructure subsystems are structurally configured to communicate information over an electronic data network.

DEFINITIONS

For convenience, further information regarding the following terms is provided below. Other and equivalent terms in this description may be used to describe similar concepts.

Patient: One or more individuals desiring or needing health advice. A may be a group, e.g. exercise class or sport team.

Caregiver: One or more individual(s) that assist the patient with their health concern. This individual is usually known to the patient, e.g. a son or daughter or parent or coach.

User: One or more patient(s) and/or caregiver(s).

Health Professional: Any individual certified or experienced within a health related field. Examples include a physician, surgeon, nurse, physician assistant (PA), nurse practitioner (NP), physical therapist, nutritional expert, paramedic etc, medic, paramedic, EMT, etc.

Nurse Hotline: A service provided by an insurance company or health related entity that provides health advice or helps connect an individual with the appropriate health professional.

Call Center: A service, that may be provided by a non-health related entity, that provides health advice or helps connect an individual with the appropriate health professional.

Provider: One or more health professional(s), nurse hotline and/or call center.

Description of Various Exemplary Embodiments

Although the disclosure hereof is detailed and exact to enable those skilled in the art to practice the invention, the physical embodiments herein disclosed merely exemplify the invention, which may be embodied in a manner not expressly described. While the preferred embodiment has been described, the details may be changed without departing from the invention, which is defined by the various disclosures and claims provided herein.

BRIEF DESCRIPTION OF THE FIGURES

FIGS. 32-35 illustrate exemplary embodiments of medical diagnostic instruments for collection of patient medical information.

DETAILED DESCRIPTION

I. Telehealth System: An Overview

Figure 1:
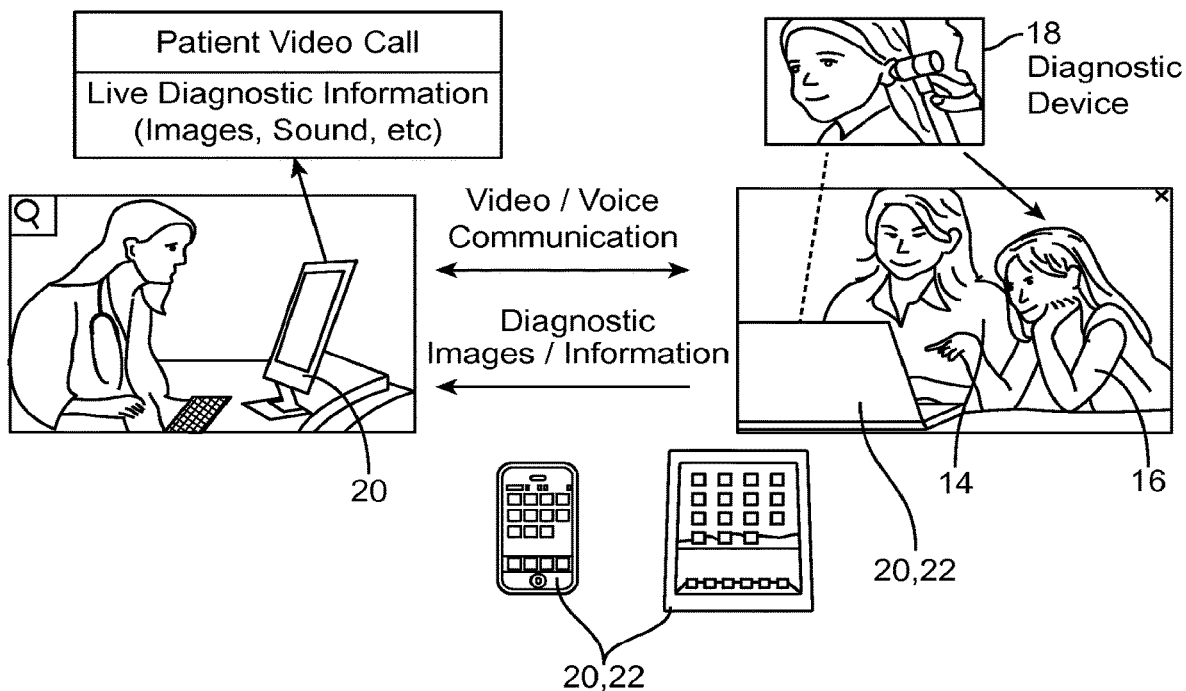
FIGS. 1 and 2 illustrate exemplary embodiments of a telehealth system in use.

The various figures described herein depict a variety of telehealth and/or other systems for remote diagnosis of health concerns. It should be understood that, while these exemplary systems include many different elements, which will be described in the sections that follow, various other embodiments of such system(s) may also include additional or fewer elements, as desired by the user and contemplated by the present disclosure. Some of these simpler or more complex systems will be discussed later.

Communication Component and Remotely Linking One or More User(s) and/or Provider(s)

A telehealth system will preferably include a method to remotely link one or more parties through communication devices and enable voice, video and/or text communication. Alternatively, a system may employ communication devices to allow a user to record and/or upload video, voice, text, background health information and/or diagnostic information and enable a provider to evaluate and provide a diagnosis or advice without live communication with the user.

The communication component(s) may take a variety of forms. For example, the user may communicate with a computer, a tablet, a landline phone, a standard mobile phone, a smart phone such as the Apple iPhone, a unique communication device specialized for use with a telehealth system, or any other device that allows recording, transmission and/or uploading of voice, video, text, files and/or diagnostic information. In various embodiments, the device will desirably allow receiving of similar information and enable the user to receive a diagnosis or advice from the provider. The provider communication component is of similar design and capability. Desirably, the provider communication device will be able to receive information from the user and transmit a diagnosis or advice to the user. The user and/or provider may use more than one communication device concurrently or sequentially. For example, a user may use a landline phone to communicate by voice with a provider and use a computer to receive and transmit diagnostic information. While the device that transmits diagnostic information may also have (or may be) a communication device, it will also be described as a diagnostic processor, which may be separate from the communication device(s).

The link between the user and provider may be created using a variety of methods. A user(s) can initiate a telehealth session by submitting a request for care. This request may be directed to a specific provider (for example, the patient's primary care physician), a limited network of providers, or it may be "crowd sourced" to any available provider, which may facilitate a more instantaneous response. In addition, the request may be routed to a nurse hotline or call center that may provide a preliminary evaluation and as necessary forward the connection to an appropriate provider.

A provider then accepts the request for care and in various embodiments a secure link between the user(s) and the provider(s) can be established. This link may be as simple as a phone call but more desirably includes a video link between the user(s) and provider(s). Also, as previously stated, the secure link may only involve the transmission of information (e.g. video, voice and/or diagnostic information) and not require "real time" live communication. The diagnostic information and/or other information such as a recorded voice and video transmission may be reviewed by a provider and/or software analysis tool offline from the user and a diagnosis or advice forwarded to the user.

Collecting and Transmitting Diagnostic Information and Relevant Medical History

The provider(s) then collect and/or review the relevant health history from the user(s) and a description of the health issue that the user(s) requires help for. If some or all of this information is contained in the user's account or in some pre-loaded form in a remote location, the user may elect to directly share this information with and/or authorize release of this stored date to the provider(s). In addition, it may be desirable that the user is able to share up-to-date (current) diagnostic information with the provider. This information may have been collected recently, over time, or during the call through the use of various home diagnostic devices. Examples of patient information can include blood pressure readings or blood glucose levels. These devices may provide the data only to the user, and the user can then share this data with the provider or allow the data to be sent or shared directly with the provider through a communication channel. This diagnostic information may also be collected through the use of diagnostic devices described in this document. Ideally, the diagnostic device is connected to a communication channel which gives the provider one or more feeds of the diagnostic data and when applicable the ability to control or refine diagnostic feeds or download snapshots or segments to allow high resolution or more precise information to be viewed. Relevant health history information may also include information or data stored or otherwise obtained from the diagnostic device or a linked device, such as geographic location data from a smartphone GPS and/or credit card or payment information from an electronic wallet, etc.

The next step is for the provider to determine a diagnosis or give advice to the user. This may include an e-prescription (which may include directions to a local pharmacy identified using GPS geographic information from the user), scheduling a follow-up consultation and/or recommending the user proceed to a doctor's office, urgent care or emergency room (which may include directions to a local service provider based on the patient's location). The user and provider then agree that a sufficient resolution has been reached. A third party may be contacted to help reach a satisfactory outcome if there is disagreement on the resolution.

C. Accounts, Logistics and Infrastructure

The final step of patient care under this exemplary system can involve termination of the consultation (e.g. provision of patient care instructions) and completion of logistics. This may include submission of an e-prescription for patient collection, processing of payment, electronic links to or emails containing the details or summary of the call, and/or creation and submission of insurance forms or other formal documentation.

In various embodiments, it may be preferred that one or more user accounts of some type are created prior to the initiation of the communication. Desirably, a user account should contain sufficient information to verify that the patient or other responsible person is able to pay for access to a provider. This account may be anonymous in nature, containing as little as payment information only, or may contain detailed information on patient history and/or a link to a patient's Electronic Health Record (EHR). Desirably, the provider account should contain sufficient information to ensure his/her identity and expertise in order to provide the requested care. This account may be part of a larger account established and maintained by a physician group, an insurance company, or other similar responsible group.

Telehealth Systems and Additional Features

There are several types of systems and features which may be incorporated into a telehealth system. The telehealth system may be as simple as a phone call between a user and a provider, or include videoconferencing and live transmission of diagnostic data such as images being captured by the user with a device. The system may also allow text and file sharing as well as links and updates to a patient's electronic health record (EHR). The provider may simply give advice or provide a formal diagnosis and submit an e-prescription. The system may also incorporate computer analysis of diagnostic data to give the user probabilities of certain conditions or be used by a provider for a more thorough analysis.

Multiple types of connections will be described, including the ability to connect a caregiver at one location, a patient at a second location and one or more providers on the same "call". The user may select specific physicians based on a ranking and pay appropriately, or offer a specific amount of money and wait for a provider to accept the fee. There may also be social/gaming/educational elements built into the system. For instance, users may wish to "crowd-source" their health issues for comments and advice from other users. Users may be offered discounts for achieving a certain level of accuracy in their feedback to other users. The system may include video-game type three-dimensional tours through or around the body with examples of health ailments and ways to prevent or treat these issues. Users may be given points and increase their status based on correct guesses for exemplary health ailments.

Several embodiments of devices, methods and systems which help facilitate the described telehealth system as well as simpler and more complex systems are described herein. It should be noted that that diagnostic embodiments may be used without a telehealth system, and that telehealth embodiments may be utilized without the use of diagnostic devices.

II. Communication Devices, Systems and Methods

Communication Component

Patient/caregiver communication devices can have any kind of structure, and can include devices which allow connection to a distant location, ideally allowing video, text, file sharing and/or other data connection. A plurality of communication devices can also be used in tandem. For example, one communication device may be used for video/voice communication, and a second communication device may be used as a channel to display and/or transmit diagnostic information to the medical services provider. Also, users may be more comfortable speaking over a landline but can see the provider on their computer (a communication device) which also serves as the data diagnostic processing unit to transfer data to the medical services provider. Examples of communications devices are provided below, and they may be used alone or in combination with other communication devices:

landline telephone, which can be used for a simple phone call or with a diagnostic device with wireless/wifi capability or other internet connection which connects to a conference call with, and feeds information to, the provider. A user can also use a landline phone with a computing device to provide video capability;

mobile telephone;

computer and telephone;

tablet and telephone;

tablet only;

computer only (with a standalone diagnostic device as applicable);

supplied device specifically for communicating with this system. Such devices are ideally suited for the elderly and they may also serve as the diagnostic computer. The device may be connected cellularly, have RF or other wireless transmission mode for connection to the Internet or to a base station connected to internet or wireless; and monitoring device or system set up in a bedroom having wide view or zoom capabilities, which may be initiated by a caregiver (e.g. for elderly patients). The system may comprise one or more cameras located in one or more rooms of the house. Users may be connected to these communication devices in a variety of ways. One way, especially useful in case of an urgent issue, is a push button device worn on the body (such as a watch, bracelet, or necklace).

Examples of a provider's communication device include:

telephone only (landline);

telephone and computing device for video or other data connection;

mobile phone only;

tablet only;

computer only;

video conference room; and simultaneous feeds to other providers for training or additional physician (e.g. a specialist)

A communication device preferably has software providing a user interface to facilitate communication, user experience, transfer of diagnostic information, recording, output/display and/or other features to aid in the telehealth service.

A communication device may also serve as a diagnostic processor (which will be explained in more detail later). This device may output diagnostic information (e.g. display images) and transfer the diagnostic information to the provider. When used in this fashion, the device may switch from video/voice communication to a voice call only while collecting and transmitting diagnostic information.

B. Systems and Methods for Remote Linking of One or More Parties

A connection between patient/caregiver and provider(s) may include any of the following steps, which may be performed in any order:

1. Request connection time, for example, as soon as possible while waiting, request first available appointment, request appointment at specific time or within window of date or time;

2. Select preferred provider (e.g. primary care physician);

3. Select preferred group (e.g. primary care and associates). Groups of medical practitioners may be available for selection, or a consumer may be able to select several individual physicians;

4. Select crowd source option, e.g., for instantaneous access, or for first to respond;

5. Select tier base of providers, wherein users pay more for higher credentials or higher ranked providers;

6. Select tiered approach for provider selection. For example, if the primary care physician is not available, the request for medical care will then pass to the next larger group after a predetermined time period, then to associates, then crowd sourced;

7. Triage by an instant connection with a nurse hotline, and then routed to appropriate provider (e.g., physician assistant, nurse practitioner, primary care, pediatrician, dermatologist, etc.);

8. Call center to answer and route call;

9. Emergency/distress request. This urgent request for assistance may be initiated with a panic button or a device worn on the body with a distress button. This button initiates a call and/or enables video devices in the area of the user. The button may also directly contact 911 services or other emergency response services. Upon initiation, the system may automatically collect data, download relevant information (e.g., GPS location information, current medical conditions such as diabetes, or current medication and prescription information) and/or maintain connection/control by remote user (e.g., medical personnel or police) throughout the entirety of the call to monitor the emergency situation and/or provide assistance;

Any of these options may be first initiated by a caregiver, and then the patient can be linked to the communication.

A connection between a caregiver and a patient may be received in any number of ways. For example, there may be a request from a patient to one or more caregivers. A request could be sent out to a single person, a few select people, or to many caregivers. Alternatively, there may be a request from a caregiver to a patient. The caregiver could open a video or communication connection without the need for the patient to "answer". For example, the care giver can activate multi-room cameras or a camera in the bedroom or a bedside device.

User Interface and Software

A provider or other party can be provided with the ability to remotely select snapshots or a short segment of video feed (or other type of diagnostic data such as sound) for high resolution download.

The user interface of the present invention allows for a simple and fast method of establishing a connection with a provider in the user's preferred method (e.g. crowd-sourced or only to primary care physician, etc., as discussed earlier). This software may be part of a standalone system or the software may provide an interface for the user which links with third-party telehealth services. This option may be especially useful when the user's insurance company already has a contract with a telehealth service but the user (and maybe the insurance company as well) desires the use of diagnostic devices described herein. The user interface would establish the easiest and clearest way for the user to manage the call and diagnostic devices while still using the third-party telehealth system as the "backbone" of the communication.

III. Diagnostic Devices, Systems and Methods

This section focuses on the different techniques used to gather diagnostic information, such as imaging and sound, as well as devices that incorporate these methods and, which interface with the human anatomy to allow reliable data capture; and connecting these devices to diagnostic processing components to transmit, output, record and/or upload the data and techniques used to manipulate or remotely control the data and/or device for higher quality and/or more efficient viewing of data which may allow a more accurate diagnosis. Diagnostic devices may be fully or partially composed of one or more features discussed in this section, including: 1) accessing and capturing components, 2) anatomical interfaces and 3) diagnostic processing components. For example, a diagnostic device may incorporate a lens and fiber optics (accessing) which channel images to a video chip (capturing) which are encapsulated within a thermoplastic shape which fits into the ear canal (anatomical interface) and attaches to a small external ear component which records images and sends the information via BlueTooth® (diagnostic processing) to a smart phone for display, recording and transfer to the internet (diagnostic processing). In this example, the smart phone may also be used as the communication component.

Diagnostic Information

Various types of diagnostic information may be desired to help provide a provider give a diagnosis or medical advice to a user. For example, a user may be concerned that his or her child has an ear infection. The provider may desire images of the ear drum, body temperature and medical history. In this case, a light sensor (e.g. CCD or CMOS video chip) may be used to image the ear drum. A standard thermometer or a device with a temperature sensor may be used to record the body temperature and transmit the data to the provider.

Another example of an illness where telehealth systems may be helpful is an upper respiratory infection. In this case, the provider may wish to know how the upper airway and/or oral cavity appears, as well as obtain lung sounds and heart rate. A device with a light sensor may be used to collect images from the upper airway and a device with a microphone may be used to listen to lung sounds as well as the heart rate. This information may then be transmitted live to a provider or uploaded for review at a separate time by a provider. The medical test data or diagnosis information may be stored locally by the user, by the medical practitioner, or by the medical care facility. The data may also be transmitted to a medical data storage location, or saved in the cloud as is known in the art.

Various other potential ailments may be evaluated. For example, images of the skin may be useful for diagnosing rashes, skin cancer or poison ivy. Images of the eye may be collected for eye problems such as red eye or foreign bodies. Images inside the nose may be useful for evaluating potential allergies or nasal infections. Sounds of the knee joint or other musculoskeletal areas may be recorded to help diagnosis arthritis or other ailments.

As will be discussed, a multitude of other data types (light, sound, electrical, temperature, strain, etc.) may be useful to examine an individual for an untold number of potential ailments.

Accessing and Capturing Diagnostic Data

Capturing devices can include a data capturing element such as a microphone or light sensor (i.e. CMOS or CCD chip). Examples of capturing devices include commercially-available and standard off-the-shelf devices as well as specialty devices. Examples of standard devices are those which may readily purchased from vendors and include smart phones, tablets and computers. Specialty devices are devices built or supplied specifically for purposes of the invention as described herein or supplied by other vendors for purposes similar to that described herein. Examples of specialty devices include devices which are similar in form to a smart phone as well devices which are incorporated into an anatomical interface and/or processing unit, which will be described in further detail later. Examples include speakers incorporated into a belt, similar in form to a heart rate monitor, and a video chip incorporated into an earphone device that is similar to an earbud or a device that includes an over ear retaining piece.

Imaging

Accessing and capturing light for displaying images can be a very useful diagnostic tool. Light is emitted by a light source (for example, a light bulb, flash, ambient, or LED) and then reflected or absorbed by the environment (for example, the atmosphere, skin, or mucous) prior to being captured, for example, using a film camera, CCD or CMOS chip. Lenses and similar components are considered herein as accessing elements. Light continues to be modified or transmitted until it hits the capturing/sensor element, for example, a CMOS or CCD chip. The light may be accessed, focused and transmitted prior to reaching the capturing element by means of devices such as lenses, fibers, mirrors and filters. The captured image may differ depending on the light source. For example, in the morning and evening, the ambient light from the sun is different and the scene viewed by an observer is different. Likewise, different LEDs or filters may be used to provide light of different wavelengths. Wavelengths outside of the visible spectrum may also be emitted, filtered and or captured. For example, certain wavelengths may be useful in distinguishing whether there is biofilm present, which is indicative of an infection, or be absorbed or reflected differently when there is fluid behind the ear drum. Variations of these features and/or methods may be incorporated into a diagnostic device.

Light may be captured, by any light capturing device at any location on the device, for example, near the end of the device, using a video chip (e.g. CMOS or CCD) or accessed at any location on the device, for example, by means such as lenses, fibers and/or mirrors and channeled to a light capturing element. Devices containing light capturing elements may take many forms. For example, light may be channeled to a light capturing element in an existing device such as a smart phone, tablet or computer. Light capturing elements may also be incorporated into specialty devices such as an earphone-type device or a specialty diagnostic instrument which may have a form factor similar to that of a smart phone. Light may be captured/accessed directly in from the end of the device or capturing/accessing elements may be configured at an angle or to the side of the end of the device.

Multiple accessing and capturing elements may be incorporated into a device. For example, two or more fiber bundles may be configured so that their ends are at different angles or locations. These fibers then channel the light to one or more light capturing elements (e.g. CCD or CMOS chip). This will allow different images to be seen. If the light is channeled to a single capturing element, two different images may be seen in the same display. Software may be used to alternately display the desired portion of the image on the full screen. Alternatively, a mirror may rotate to alternate the displayed images from the two or more different fibers. If the fibers are positioned at left and right positions, the two images may be combined in order to create a 3-D image. If a single capturing element is used, software may be used to differentiate the images and then create the 3-D image. Alternatively, straight channels and/or channels and mirrors may be used to transmit the light to the light capturing element without the use of fibers. Alternatively, light capturing elements may be located the end of the device and capture the light at that location, at multiple locations and/or multiple angles.

Light may be supplied in a variety of ways as well. Light may be emitted from a light source (e.g. LED) at the end of the device or light may be transmitted to the end of the device. For example, fibers, mirrors or straight channels may be used to transmit the light to the desired output location. Various filters may be used to change the emitted wavelength and/or more than one color or wavelength light source may be incorporated into a device. Filters may also be used just in front of the capturing element and/or software used to modify the exposure so that certain wavelengths, brightnesses or other types of image variables are modified or restricted from the image. Light may be output in a variety of geometrical manners as well. For instance, light may be output in a ring surrounding the video accessing and/or capturing elements, emitted from a single location adjacent to the accessing/capturing element(s), or from more than one location relative to the accessing/capturing elements.

Multiple accessing and capturing elements may be positioned to image different areas. For example, one may desire to see an image of the skin, throat or ear while also seeing a more contextual image, such as how the device is being used and positioned. An example of one configuration is using one of the cameras of a smartphone to capture an image of a child, and light is channeled using fibers from the child's ear to the second camera on the smart phone. Imaging accessing and capturing elements may also be positioned to capture images in different locations of a desired target area, for example in the oral cavity and then further away in the back of the throat. Imaging elements may also be located close to one another but facilitate capturing images at different locations by having different focal lengths accomplished through lenses or other components, for example using software that can focus an image after capturing when used with a capturing element that identifies angles of the captured light, e.g., using Lytro camera technology.

Various methods may be used to maintain a clear image. For example, air or water may be channeled to the end of the device to maintain a clean and clear end of the accessing element (such as a lens) or circulated around or behind the lens or other accessing or capturing element to prevent condensation or fogging. Anti-fogging fluid may also be applied to the device prior to use.

An accessing element may also be expandable. For example, a tube may be compressed for accessing a location and then expanded (for example, by inflation) to expand the diameter or size and therefore access a greater imaging area. Another example of an expandable device is one constructed of a central expandable member with accessing and/or capturing elements surrounding this member. When the central member is expanded, the surrounding elements are pushed out, accessing a larger area. Expandable members may also be used to change the position or angle of the accessing/capturing elements. For example, an expandable member may push the accessing/capturing elements up into the top of the oral cavity or to one side of an ear canal. Similar techniques may also be used for light sources.

Accessing and/or capturing elements may be configured for flexibility to allow conformance to a desired location (for example, an ear canal) and/or incorporate elements that allow the flexible elements to be manipulated. For example, a fiber bundle may be steered by a user in a fashion similar to endoscopes, or be remotely steered by a provider or other person. Alternatively, just the tip elements (such as a lens, mirror and/or light sensing chip) may be steered or manipulated. Manipulation of the elements may include modification of the focal length.

Other imaging techniques may also be incorporated into diagnostic devices. One example includes ultrasonic imaging.

Sound can be detected using a diagnostic device using any number of techniques. Sound may also be accessed and captured with a variety of methods. As opposed to light, sound may be captured through the air and/or captured after being transmitted through fluids or tissue or devices. Microphones may be mounted on probes to record sounds when the probe is in contact with the body or when placed into cavities such as the mouth. These microphones may be placed at the tips of the probes or away from the tips and record vibrations transmitted through the probes. Microphones may also be mounted on or in surface mounted devices. Examples of these devices include pads placed on, attached to, wrapped around or worn on a body part such as a device similar to a knee brace or a belt or a vest. These devices may be designed to capture sounds such as those emitted by joints, the heart and/or the lungs or airway. Microphones located at or close to the surface of the device near tissue may capture more localized sound while microphones located deeper in devices and further from tissue may capture sounds from a larger area. Sound may also be accessed at a distance and channeled through a tube(s) to a microphone in a capturing unit.

Sound accessing elements may be "open", or natural, or constructed similar to a diaphragm. This diaphragm may be designed to conform to the desired area for a more thorough and reliable contact area and/or to amplify the sounds and/or to collect sound from a broader area. The diaphragm may be similar to that of a stethoscope. It may attach to a capturing device with a microphone, such as a smart phone or a small unit with a microphone that transmits the sound, preferably wirelessly, to a diagnostic processing device (i.e. a smart phone). Alternatively, the diaphragm and microphone may be incorporated into the same unit which attaches to a diagnostic processor which transmits the data, preferably wirelessly, to another diagnostic processing unit such as a smart phone which may output and/or store and/or send the data through the internet. This diaphragm, with or without microphone, may attach to the same diagnostic processor as the light accessing element.

Sound may also be filtered and/or amplified. For example, when using a diaphragm and stethoscope type device, sounds relevant to the heart and/or lungs may be filtered and amplified while other sounds may be filtered and discarded. This filtering may be done by the diagnostic processing unit or at the provider end and may be controlled by the provider. Also, microphones with different sensitivities may be used in order to collect a larger range of frequency of sounds and/or larger range of amplitudes. Once again, filters may then be used.

Movement can be detected or captured using any kind of motion-detecting device. Examples of such devices are strain gages and accelerometers. Pressure in tubes can also be used to detect expansion/contraction, and pressure or sound changes in bags/compartments can be used to detect motion, for example, devices placed under a mattress. Such devices can also be placed around a patient's legs, knees, or other body part for detection of muscle or limb motion.

In certain embodiments, GPS units can be used to detect motion. External stereotactic devices, which devices track three or more points, can be mounted on various worn items; or wrapped on or affixed to a patient's legs, vest, belt, or other part of the body or clothing.

Muscle spasms or tension can be monitored to detect or diagnose conditions such as headaches which are often musculoskeletal.

Headband or bandage-type devices which contain strain gauges or other mechanisms can be used to detect motion and/or strain. Video cameras or motion sensors such as the Kinect device can also be used. Microelectricalmechanical (MEMS) sensors and devices worn on the body containing MEMS sensors (e.g., vest, belt, wraps, leggings, etc.) are also useful.

Reflexes can be detected or captured, for example, by determining a patient's quickness in pushing buttons or other responses. The responses can be tested in a gaming environment which can be hardware or software-based. Devices can also have a mechanism for hitting nerves or other tissue to elicit a reflex response. The diagnostic instrument may be integrated into a knee or elbow wrap or mount.

Patient health can be assessed using electrical-based diagnostic equipment to detect or diagnose conditions such as eye movement; hydration (resistance), and fat content (resistance), via electrooculography, electroretinograms, EEG, EKG, and/or EMG.

Temperature can be detected using various methodology, such as infrared, e.g. ear temperature or skin surface; or conductance; for example, using a standard thermometer. Relative temperature can also be used between different body surfaces or regions.

Touch and pressure can be sensed using gloves with pressure sensors to indicate how hard a patient is pressing on something. Such sensors may give a numerical or other scale feedback or provide a tactile output through device on the provider end. For example, a glove with pressure compartments may be modified to duplicate the pressures felt/recorded on the user end. Socks with pressure sensors can be used for gait, or for podiatrist assistance.

Other senses that can be measured include kinesthetics (relative position of body parts—e.g., a patient is asked to touch his or her nose with a finger with the eyes closed); or balance, magnetic/electrical fields, and pain.

The invention can also be used to measure or monitor standard diagnostics or vitals. That is, the invention can be used to obtain standard diagnostic information and vital signs such as pulse, oximetry, pulse oximetry, $CO_2$ blood levels, cardiac output (arterial pulse), heart rate, glucose monitoring, blood pressure, and weight.

Other tests or diagnostics that can be used with the invention include, for example, swabs or blood pin-pricks. Third party diagnostic devices and tests can also be incorporated through release of standard interfaces or programming information.

Methods and types of diagnosis can be based on any combination of diagnostic information. There are numerous health ailments which may be diagnosed using any one of or a combination of the techniques discussed above. Below is a short list of examples.

1. Imaging of the ear drum for ear infections. Such diagnostic tests may also take an infrared temperature reading;
2. Listening to sounds of four quadrants or lung on the back of a patient. Such tests may help to diagnose asthma or a respiratory infection;
3. Imaging of the skin to detect skin cancer, rashes, poison ivy, or other such ailments;
4. Images of the mouth and throat for upper respiratory ailments/infections;
5. Epiglottitis by listening to sounds near trachea; and
6. Diagnosing flu and common cold, using data such as body temperature, images of the throat and listening to lungs.

Anatomical Interfaces for Diagnostic Devices

Anatomical interfaces for diagnostic devices can have any shape or structure. Examples of devices with anatomical interfaces include otoscopes, rhinoscopes, and throat visualizers. While interfaces may be discussed in reference to a specific diagnostic technique and/or device, such as an otoscope for imaging the ear, similar anatomic interfaces and/or devices may be used to collect any type of diagnostic information. An example is an anatomical interface for the ear similar used to collect temperature information rather than imaging information. Anatomical interfaces may include elements to collect more than one type of diagnostic information. Examples of such devices will now be discussed in further detail.

An otoscope may have features such as a flexible extension for easier insertion into the ear and for alignment to the ear drum and to conform to the ear canal. This extension may have a feature to prevent over-insertion or to limit the amount of force that is encountered. For example, the extension may be spring loaded and able to fully or partially retract depending on the forces encountered. This retraction, or force limiting mechanism, may be incorporated into a more rigid extension as well.

There may be a soft outer material on the extension for comfort during insertion and while imaging. These may also be more rigid internal material to maintain a desired shape. The extension may have a stop that interfaces with the patient to prevent over insertion into the ear canal. In one embodiment, the stop presses into outer ear and does not compress tissue into ear canal. There may also be hole to allow air to escape during insertion and imaging, or to prevent echoing or other bothersome noises.

The stop can be incorporated into a disposable sleeve, or it can have a shape similar to an earphone bud, or a cup around the ear. The diameter of the extension can also increase, thereby functioning as a stop in the ear canal. There may also be adjustable stops or different-sized sleeves to fit different ages.

Ear buds that snugly fit in the ear such as the Doc's Ear Plug, may have an extension into the ear canal. Over ear devices similar to ear phones can also serve as a stop or to provide alignment and/or to hold an imaging device in place.

A small bud or a bud with an over ear holder can have one or more small flexible wires connecting the bud to another device, or the bud may be self-contained and having RF, wifi, or other wireless communication link with a diagnostic computer and/or processor. Such devices allow significant motion and hands-free capturing of data, and such embodiments help with freeing up a user to manipulate the ear. There may also be an LED at the tip or channeled from the outer ear into the tip.

Screw type or other adjustments can be used to change the length of insertion, and a balloon or other dilation method can be used to stop and hold the device in place.

Such devices fit into the ear and align the capturing and/or accessing elements. Ideally, the device will be able to image the ear drum with minimal or no manipulation of the ear. The capturing/accessing elements may be offset from the central axis of the ear canal and/or angled relative to the axis.

The extension into the inner ear may be formed of a polymer or other material. A lens can be in a central position, or it can be offset, and optionally offset posteriorly. This extension may dilate the canal if desired.

There may also be different attachments for the left and right ears, and such attachments may connect to a capturing device and channel images from the tip. A tip which rotates to fit into and align elements with left and right ear canal and ear drum is also possible and within the scope of the present invention.

Dilation of the ear canal is also possible by means of a balloon or other inflation device. This dilation may push imaging, light, or other channels outward for a larger viewing field and/or additional viewing angles.

Multiple attachments to fit different ear sizes or patient ages are possible and encompassed by the present invention. Such pieces may be very inexpensive and therefore disposable. There may also be moldable attachments for patient-specific fittings.

There may also be an extendable piece or longer extension fittings to see deeper in the ear canal for better clarity and/or to get past ear hairs. A head band, hat or similar retaining device can be used to help secure and hold the ear imaging device in place.

Many of the above features will also be useful in other anatomical interface embodiments.

For example, a rhinoscope may consist of a nose plug with various insert lengths and shapes, and a soft tip. There may be a soft outer material surrounding a more rigid inner material that maintains its shape. There may also be dual tips for both nostrils, which can be useful for imaging nasal cavities.

The invention also provides for an attachment to look into the throat. The attachment may consist of a narrower fiberscope when viewed from the side that more naturally conforms with the shape of the oral cavity, optionally with a mouth piece to depress the tongue and to open the oral cavity for better imaging. The mouth piece may be similar in shape to a pacifier. The attachment may also have a slight downward curve to depress the tongue and to provide a downward angle further back in the oral cavity to image the throat. Similar to a pacifier, the outer material of this oral device would preferably be soft and/or semi-compressible. The oral device may have any shape, and in one embodiment is oval in shape, as pacifiers generally are, to more naturally conform with the oral cavity. This oral device may be generally flexible in nature and bend with motions in an oral cavity should a patient, such as a child, resist to the device being used.

The invention also provides for a dermatoscope, which can maintain a specific distance from the object to be imaged to enable measurements over time. A dermatoscope may incorporate an object of known size for reference in images obtained.

The invention also provides for a heart rate (HR) type belt or similar device which can be used to detect breathing sounds and to listen to the lungs as well as to check the heart beat. Other devices to detect sounds are a vest with microphones, and a small interface similar in size to the end of a stethoscope but attachable to a smart phone or other device with a microphone or containing a microphone and interfacing with an adapter to send the sounds to a computer.

Certain embodiments of the invention provide for a method to detect internal sound by external diagnostic equipment. One purpose is to help give a sense of what the patient feels, and such embodiments are particularly useful for orthopedics.

An example of a device having these features is a brace for the back, knee or other area to pick up sounds (ideally internal) that may alone provide a diagnosis or provide reassurance when combined with other diagnostic data such as images.

The invention also provides for a small probe inserted through the topmost layer(s) of the skin.

The invention also provides for a probe which may be inserted into a body cavity (e.g., oral, stomach, intestines, etc.). Examination of the oral cavity may help with GERD diagnosis. The obtained data can be used to correlate sounds with specific ailments or to narrow down possibilities or identify potential issues.

The invention also provides for a device for measuring temperature, which may consist of an IR detector built into an ear bud or similar device. The ear device may be held in place with a hat or head band. Alternatively, the temperature detector can be built into a head band or hat device with skin contact probes, and be optionally positioned on a patient's forehead area.

The invention also provides for a device for measuring oxygen saturation, for example, in the form of a finger or toe attachment.

The invention also provides for a device for measuring blood pressure, for example, for placement on a patient's wrist or arm.

The invention also provides for a device in the form of an eye piece (e.g. a cup-type shape) to provide safe imaging of eye and surrounding tissue.

Particular embodiments of capturing devices have a thin sleeve and/or covering that is disposable and which maintains a barrier as well as providing padding for comfort during a medical examination. There may also be stops to prevent over insertion (e.g., for an otoscope). Adhesive patches for skin mounted or contact devices can be used. The capturing device may also have a moldable interface.

The capturing device may also be integrated with a device to view, hear or otherwise observe or sense the diagnostic information. This may be a diagnostic processing unit as discussed later, or a simpler type interface such as an optical viewport to see the images through the diagnostic device. This device may or may not include components allowing storage or transfer of the diagnostic information. Such components may include software, mechanical elements, and/or other human interface to manipulate output.

Diagnostic Processing and Link to Diagnostic Device

The diagnostic processing components (sometimes referred to as diagnostic processors, or processors or processing components) allow for receiving, transmitting, outputting and/or recording diagnostic information and/or uploading the information to the internet. The information may be stored at a remote location if the information is being uploaded.

The diagnostic processing components may communicate with the diagnostic accessing and capturing components through a wired or wireless connection. Examples of wireless communication include RF (e.g. Bluetooth), wifi and/or wireless phone technology. An example of such a configuration includes a small wireless transmitter which attaches to and is wired to an image capturing device and transmits (preferably wirelessly) the data to a smart phone, tablet or other computer. This computer may then display the images, record the information and/or upload the information to the internet.

All processing components may be integrated into a single device, for example, a tablet, smart phone or other computer. An image accessing device with an anatomical interface is then positioned in front of the computer camera. The computer is then able to capture, record, display and/or upload the information. This computer may also serve as the communication device.

The accessing and/or capturing components may also be mechanically attached to the processing components. An example of this is a cradle with handle and a device with an anatomical interface housing a lens, video chip and RF transmitter, as well as other electronics. The cradle holds a tablet, smart phone or other computing device. The images are then sent (preferably wirelessly) from the device to the computing device in the cradle for displaying, recording and/or uploading. In another embodiment, a folder, portfolio, or carry case may hold a computer tablet on one side for communication and a smart phone or tablet on the other side to receive, record, display and/or upload the diagnostic information.

Diagnostic Processing Components

Part or all of the diagnostic processor may be the same as the communication device (e.g. laptop, tablet, smart phone) or other existing computer device (e.g. desktop, second communication device).

The diagnostic processor engages in wired or wireless communication to a diagnostic capturing device. The diagnostic processor may also serve as the diagnostic capturing device, for example, having an anatomical interface which attaches in front of a smartphone camera.

The diagnostic processing components may be built into the diagnostic capturing device. For example, a wireless transmitter may be attached and wired to a capturing device. The diagnostic information is uploaded directly to the internet and then may be downloaded to a communication device.

Alternatively, the diagnostic processing components may be located in another device, such as a base station. The base station can be located anywhere in the home or other facility, and is typically plugged in a power outlet and connected to the internet or a wireless service. This station communicates with and receives the information from the diagnostic capturing device. Information may then be transferred to a communication device and/or directly uploaded to the internet. If directly uploaded to the Internet, the information may then be downloaded for display or other output in the communication device.

The diagnostic processing unit can also be a local "box" that communicates/connects to the diagnostic capturing device. The diagnostic capturing device may transmit the information wirelessly (e.g. RF) to the local box or be connected with a wire.

The local box may optionally be configured to display diagnostic information. This may attach directly to the diagnostic capturing device, be hand held and allow moving and placing the diagnostic capturing device as desired Other form forms include a watch or a flexible display that may be unfolded if applicable and placed in a convenient location. The local box or similar device is usually situated to be mechanically and/or electronically attached or linked to a communication device as previously discussed.

The device can also serve as a communication device, particularly if it has a display screen.

The local box may transmit information to a smart phone, tablet or other computer for outputting, recording and/or uploading the information.

Multiple devices and communication methods may be combined. For example, the diagnostic capturing device may have diagnostic processing components built in to record the information and/or display the information and also transfer the information to a local computer or communication device as well as directly transmit the information via the internet or wireless phone technology.

The local box or electronics may allow attachment to a multitude of diagnostic devices and be able to transmit the data to the internet, the communication device or other device as previously described.

The diagnostic processing components may also have a mechanical link for information transfer. The diagnostic accessing device may have a hollow tube for transmission of sound or fiber optics for transmission of images to a diagnostic processing device. The diagnostic processing device may have the hardware required to capture and process the information. Examples of hardware include a camera and/or microphone, and may include a cradle or other attachment to help align parts for adequate capturing of the diagnostic information.

The diagnostic processing component(s) may be able to communicate/connect to third party diagnostic devices as well. For example, a local box as previously described may communicate with heart rate monitors, pulse oximeter, scales, blood glucose monitors, etc.

Other features of a diagnostic processor and/or capturing device may include a conventional camera, a microphone, and/or a recorder. These elements may include a mechanical and/or electronic link between the anatomical interface and the camera or microphone to provide for transfer of the diagnostic information.

Examples of Diagnostic Devices and Additional Features

Different devices which are created by combinations of disclosed features and components discussed in above sections can allow for accessing and capturing of data, an anatomical interface, and diagnostic processing.

A diagnostic device may have channels for secondary uses. For example, an otoscope for visualizing the ear drum may have a channel to allow air to be inserted into and pressurize the ear canal to visualize motion of the ear drum. Alternatively, additional diagnostic techniques which are not discussed herein may be incorporated into any diagnostic device.

A diagnostic device may have multiple diagnostic capturing elements. The diagnostic device may be held in place on the patient's body using any generally available or suitable means. For example, an otoscope may have an image capturing device and a temperature probe (such as an infrared thermometer). This ear device may be held in place with a head band, hat or similar retaining device. The temperature reading apparatus may also be positioned in the hat or head band rather than in the ear piece, and have skin contact probes which are ideally positioned near or on the forehead. Temperature readings may be recorded both within the ear and on the forehead to increase the likelihood of recording an accurate temperature.

Kits containing more than one type of diagnostic device and/or anatomical interface are provided by and encompassed by the present invention.

Diagnostic devices may have features to make them more comfortable and/or acceptable to the patient. Such features may include, but are not limited to a speaker in an ear piece (e.g. otoscope) playing soothing sounds or music that the patient finds enjoyable or vibration in a skin interface device (e.g. dermatoscope). An oral device or device to look into the throat (e.g. laryngoscope) may include a video screen situated in front of the patient to play videos for the patient and/or include a pleasant tasting mouth insert or the ability to apply a pleasant taste to the oral device or laryngoscope.

As illustrated and described herein, many devices are formed to be familiar to the user and therefore make them more comfortable and pleasant to use. For example, an ear imaging device with an earbud or over ear engagement member are similar in feel and use to headphones. The user may feel comfortable using such device and requires little or no instructions on using it. Similarly, an oral device for capturing diagnostic information, such as images, may be shaped in an oval form. This oval shape will more naturally conform to the mouth. The oval shape may resemble a pacifier or have another known shape. Users may feel more comfortable and safe using a device on themselves or their child since the device resembles a product they have used before. Further, devices are preferably constructed to resemble consumer products rather than medical devices to provide a more pleasant experience and also decrease the time and effort to learn how to use the device.

F. Remote Control and/or Manipulation of Diagnostic Device and/or Diagnostic Information The invention can provide live feeds with the ability to request a snapshot or segment in higher resolution. The invention also permits low resolution viewing of large files such as MRIs, and the ability to request high quality images of select images or parts of images.

In certain embodiments, the invention can pull information from electronic health records and/or a central location of stored information. Such data files can be reviewed in low resolution and then selected files or portions of files can be retrieved for high resolution download.

The invention also provides the ability to modify device settings, such as filtering of sounds, zooming cameras, selecting which angle view is best, changing filters of images, increasing/decreasing electrical power, changing light source, selecting a camera, or modification of any other option previously discussed. There is also the ability of remote monitoring and/or control of a user device.

There may also be controlled articulation of a device, to change an angle or other shape to help navigate or align an instrument, or to change a tip angle or angle of elements such as a mirror or video chip.

IV. Accounts, Logistics and Infrastructure

Examples of User and Provider Account(s)

Several kinds of user accounts and provider accounts are possible in accordance with the principles of the present invention. There may be an anonymous account, in which billing and personal information is processed by a company or service, or a third-party service or telehealth service, or by the company described within), but the provider does not know the patient's identity and health records are not updated. This option allows advice only, and no prescriptions.

There may also be a basic account with consumer identification. Basic health information/background is collected during call, similar to a visit to a pharmacy clinic.

There may also be a basic account with past medical history completed for use with this system. Certain information, for example, a simple health questionnaire, remains separate from other patient records.

There may also be an account which provides for integration with the patient's existing Electronic Health Records (EHRs). Such accounts may pull out a subset of basic health information only for purposes of use in conjunction with the current sick call to keep the majority of the information private. The patient or caregiver decides what kind of information or which categories of health information is shared. This sharing could be done for each sick call.

Shared information may optionally be linked to a third party EHR. An EHR can be managed within this system. Health information can also be sent as required to update the patient's record(s) and pulled from other records as necessary.

Accounts can be created by the user, the user's health insurance, employer, family member, or another interested party.

An account can be created with health insurance information, or the account can be completely private and provide for separate billing via a self-pay model.

Patient accounts will be determined in accordance with particular implementations of the invention. Such accounts are envisioned to be fully HIPPA compliant, and the consumer controls and chooses what information is shared and with whom. Permission from the patient may be transmitted with any medical data and/or via a separate/independent transmission method or file.

Provider account(s) may include call records maintained (e.g. user satisfaction), and provider credentials.

Completion of Communication

Both parties may first need to agree that an acceptable resolution has been reached prior to completing the call as well as agree to which information may be stored prior to the uploading and sharing of information to an EHR or updating of any other record.

Billing and Insurance

The invention is amenable to different kinds of billing and insurance modes. For example, there may be a self-pay mode, or the user or provider can bill an insurance company and generate the relevant forms.

Communication Security and Methods of Transferring Information

The invention can use existing technology/company/software such as Vidyo, or such technology can be created from the ground up in-house.

E. Recording of Information

The invention can provide for multiple record storage options. For example, the invention can record entire communications and all imaging/collection of diagnostic information, or the invention can record only short segments or snapshots of diagnostic information selected by the provider and the final diagnosis and/or advice given. Alternatively, the invention can store only a form containing health history and a written diagnosis by the provider, with or without images. Prior to providing or receiving any service, the patient/consumer and health care provider can agree on completed review and storage of information.

F. Database Management

Database management for a particular implementation of the invention will generally be conducted in accordance with industry practices and regulations.

G. Interfacing with $3^{rd}$ Party Software and Hardware Including Electronic Medical Records (EMRs) and Diagnostic Devices The invention can also interfacing with third party software and hardware providers, including those providing or storing Electronic Medical Records (EMRs) and diagnostic devices V. Telehealth Systems and Features Telehealth systems in accordance with the present invention permit the linking of two or more parties at remote locations to aid with or monitor medical conditions. The connections may be in the form of a voice call, video call and/or text communication or any of these with the addition of sharing information such as photos, files and/or diagnostic information, collected previously and/or collected during communication.

Communication methods may include cellular/mobile telephone, through the internet, via satellite, landline or any other technology enabling communication protocol.

Telehealth systems utilize diagnostic or health information collected with a variety of methods or available from previous health consultations. A third party device or a diagnostic device described herein, or other information such as xrays, MRIs, blood tests or information contained in an electronic health record can be utilized.

Telehealth system in accordance with the invention may involve an official diagnosis, e-prescriptions, billing (individual and/or insurance), creation of insurance forms and/or updating EHRs.

Such systems also use software and/or user interfaces to facilitate capture, output (e.g. display or sound), transfer and/or recording of information.

Infrastructure, including servers and databases, can be purchased commercially or custom-designed, depending on the implementation of the invention.

Health care providers such as physicians or other professionals may be ranked by education, experience, user satisfaction or other means by which a user may wish to select a provider. Users or insurance companies may pay different amounts depending on the rank of the provider, or based upon prior negotiation.

Certain embodiments of the invention may be desirable for use in a gaming, social, or educational setting. For example, the invention can provide a 3D tour through the body and participants would guess medical solutions or diagnoses based on real data or examples for each location/area of the body. Users may get points and compete against others.

There may also be crowd-sourcing to other users for opinions without provider input. Users may compete against each other and be ranked for knowledge which may help in the probability of obtaining correct advice from the crowd.

The invention can also use real data for educational purposes with an interactive interface, e.g., a 3D tour through the body. The invention can also include demonstrations and illustrations of how a health ailment may have been caused and how to prevent or treat that condition.

Certain embodiments of the invention can be used for auto detection of ailments, for example, ear infections and progression of moles, and the invention can give the probability that the patient has the illness with or without an additional provider consultation. Software and analysis can be done on the user device and/or as a "cloud" service.

There may also be crowd sourcing for two or more opinions from providers. Such embodiments may be particularly applicable to lower income countries or those having lower provider cost (such as India) and for easily-diagnosed ailments requiring only an image or similarly simple sharing of diagnostic information. This would give a potential for extremely short provider review times, potentially in just 10 seconds.

The invention can also be used to solicit bids from providers for consultations, surgery or other care. A user may also offer a set amount for diagnosis and treatment, and providers may choose to accept the user's offer or not.

The invention can also be integrated with outside diagnostics facilities, for example, for lab tests or culture testing; to enable users to send samples such as blood, mucous, and skin shavings for analysis; and to schedule appointments for blood draws/testing or imaging tests such as xray or MRI.

Contacts between patients/caregivers and medical care providers can be in any form, such as the following:
 1. Direct peer to peer or through central server/gate or simultaneously peer to peer and to central location;
 2. Caregiver and patient;
 3. Patient and provider (or nurse/call center for routing if necessary);
 4. Patient, caregiver to provider(s)
 5. Caregiver to provider and separately to patient;
 6. Patient separately to caregiver and provider; and
 7. Any of the above with a facilitator such as a nurse or other trained individual at a call center A non-limiting list of examples of sick calls or requests for medical services can include requests for second opinions; treatment of acute ailments; treatment of chronic ailments; requests for follow-up appointments; scheduling physical therapy; monitoring, which can be initiated by caregiver and not require an active answer by the patient; fitness or wellness visits; and emergency and other urgent medical calls.

The invention can be provided to consumers in numerous ways, such as by health insurance companies, employers, through partnerships with health IT companies, or directly to consumers.

Different kinds of systems are possible within the scope of the present invention. For example, there may be a basic system, which provides telemedicine with at least voice capability and optionally video capability to enable remote diagnosis and prescriptions as necessary. There may also be diagnostic device services, in which the invention provides the ability to capture and send medical data and information from a patient to a health care provider. The systems may also have the ability to transfer a live feed of diagnostic information from the patient to the provider, or the ability for the provider to select snapshots or short segment video to download in high resolution from the diagnostic device.

There may also be a hardware or software interface to allow connection of any diagnostic device, e.g. for example, from a third party. These connections can be live feeds or collected over time such as blood glucose or heart rate and input by user, for example, by typing blood pressure readings into a diagnostic device. For live feeds, in one embodiment, the invention allows for recordal of information and data, and for remote transfer of high quality images.

VI. Systems with Therapeutic Elements

The invention may also be in communications with medical devices which provide remote therapeutic elements or services to a patient. Examples of such devices are massage devices or muscle or nerve stimulation devices. The medical provider can send remote instructions to these devices so that the patient can obtain therapeutic treatment.

As described herein, various embodiments of the disclosed systems and methods significantly improve efficiency for patients, clinicians, health system managers, and third party payers. The stored patient information allows reviewing clinicians to see the patient examination and glean valuable information that a previous clinician might have missed during a routine examination. Moreover, multiple clinicians and/or specialists can access the patient information simultaneously and/or sequentially, allowing additional reviews to review the data and reduce the chance of something being missed or overlooked.

The system can include features that allow consultants to review the comments and recommendations of other clinicians. In doing so, consultants may be exposed to the thoughts of other clinicians, which in turn can broaden or focus the clinical impressions more accurately, and again reduce the chances of error or misdiagnosis. Such review will normally be done within the data sharing permissions set by the patient, as well as within the scope of medical record sharing laws and regulations.

Various features of the disclosed system may encourage patient participation and involvement. The patient has opportunity to see his or her case, actively monitor the progression and assessment of the information by medical professionals, and review the various comments and recommendations and actively participate in his/her case. This may result in a more informed and involved patient, and can significantly increase patient satisfaction with the medical care and response.

In various embodiments, the user's initial patient information and treatment request creates a query that becomes available to the medical professionals (e.g., consulting clinicians) via a secure web portal or other format. The system provides the medical professional with the relevant patient data to be used in providing recommendations regarding the patient condition, assessment and/or treatment. The medical professional can review the query on-line at any time after it has been posted and can record his/her observations and recommendations into the query file as necessary and/or desired. Depending upon the patient condition and/or complexity, an initial assessment can be rapidly completed, for example, in 15 minutes or less, by properly trained personnel such as nurses, initial assessment technicians, or first responders. Such initial assessment may take significantly less time than needed for a clinician to evaluate the patient in person. For patients requiring further in-depth assessment and/or analysis, their queries may be forwarded to a relevant specialist, while less complex queries can be addressed and responded to by a wide variety of less-expensive clinical specialists. This can significantly reduce the costs incurred to evaluate the patient, which may result in significantly lower costs for the patient and/or payor. In addition, the patient does not need to directly meet with clinicians individually, which may significantly increase the convenience and accessibility of healthcare.

Various features of the disclosed systems and methods may further facilitate the collection and recordation of patient demographics, medical histories, complaints, illness histories, height, weight, identification (e.g., fingerprints, facial photographs, DNA or blood type information), patient statements, video exam sequences, and physical characteristics such as physical inspection results, thermal imaging, palpation, strength, sensation and reflexes. In addition, various information relevant to the complaint can include links to electronic medical records, links to imaging databases, various clinical comments, and billing information. Patients can give permission for the attending clinician to access their stored health records. The clinician can provide the most rapid physical examination if a patient's records are all available electronically. Nevertheless, the invention can also be highly effective to start developing a patient's electronic health record.

Use of the various systems and methods disclosed herein may be of interest to health systems administrators as it may facilitate a hospital or clinician group's expansion of their service area, attract patients to their treatment facilities, promote utilization of participating providers, create multiple revenue streams, and may be a powerful marketing tool. In various embodiments, the systems add efficiency and increase clinical productivity.

In various embodiments, researchers may utilize various database information which may include data mining features, standardization of examination methods, and an objective documentation format. Similarly, health care professionals and/or educators may utilize various features that provide a rich educational format that can be accessed by students seeking to gain knowledge regarding the evaluation and management of health issues. The patient information files may be archived and used to provide exposure to a wide variety of cases and demonstrate various pathologies to students who might otherwise go years before seeing an example of certain variant conditions. In various embodiments, a multidisciplinary consultation feature can be provided that allows exposure of patient information to a variety of medical perspectives. Such data sharing will normally be used in accordance with local privacy laws.

Various features of disclosed embodiments offer significant direct cost savings, which may be realized when an emergency room or full office visit consultation is avoided because the information is available via the system. The system saves time because the patient does not have to wait to attend a variety of appointments and each clinician (if multiple medical professionals are required or desired) can view the patient information remotely on his or her own time. In addition, multiple consultations and opinions can be collected via the system simultaneously.

Advantageously, the system can increase quality by making multiple opinions available to the patient, which can increase patient responsibility and autonomy and facilitate greater levels of involvement in patients' own health care. In various embodiments, patients may be given the option of selecting a desired clinician or clinical specialty that they would like to consult on their patient information. The patient can directly review the various opinions and recommendations collected in the system and make their own choices about how they would like to proceed. Patients can increase their understanding and knowledge of their condition by allowing them (or anyone else they so choose) to view their personal examination compilation in detail. In addition, the system allows third party payers to have a more complete and accurate assessment of the claimant's examination compilation.

The present invention will now be described with reference to the Figures.

Figure 2:
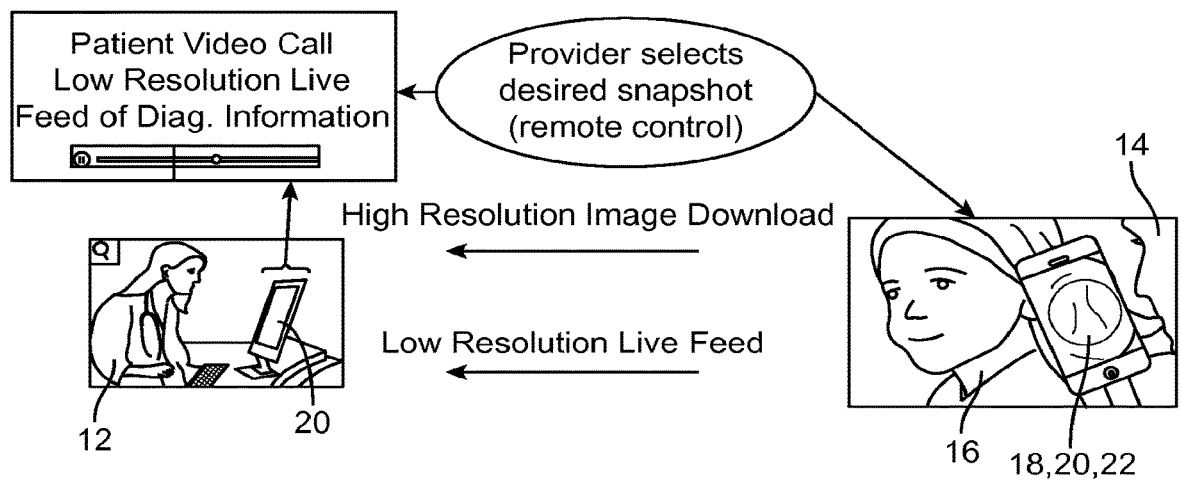

FIGS. 1 and 2 illustrate exemplary embodiments of a telehealth system in use in accordance with an aspect of the present invention. FIG. 1 illustrates a caregiver and a health care provider engaged in a video call, thereby interacting in two-way video and voice communications. A diagnostic device in accordance with the present invention has been inserted in to the patient's ear, and the diagnostic device acquires medical status data, including diagnostic images, and provides this information to the provider. During the video call, the provider can request that the caregiver or patient provide additional medical information or adjust the settings or placement of the diagnostic device. Although the figure shows the caregiver using a laptop computer and the provider using a desktop computer, the caregiver and provider can use other kinds of computer systems, such as the illustrated smartphone or tablet computer. In certain embodiments of the invention, caregivers and/or providers will install an application or an app on their devices to communicate. In view of current U.S. federal privacy laws, it is expected that all communications between a provider and patient/caregiver will be done over a secure electronic connection.

FIG. 2 illustrates an exemplary embodiment of the invention which provides for a plurality of data feed options to the provider from the diagnostic device. In the illustrated embodiment, the provider can choose to receive one or more high-resolution images via download, or the provider can receive a low-resolution live feed. The provider has the ability to manipulate the diagnostic information and/or the device by a remote control feature. In this specific Figure, the diagnostic data can be fed live to the provider at low resolution for seamless transfer and communication. The provider may select segments or snapshots of the diagnostic feed which will be downloaded to him or her at a higher resolution. The full stream of higher resolution data can be stored on the user's device and/or at a central location, and accessed by the provider for high resolution snapshots/segments or for later review. The provider may use the remote control feature for other actions, such as but not limited to focusing the image, controlling tip deflection or the direction of an imaging device, and filtering sounds.

Figure 3:
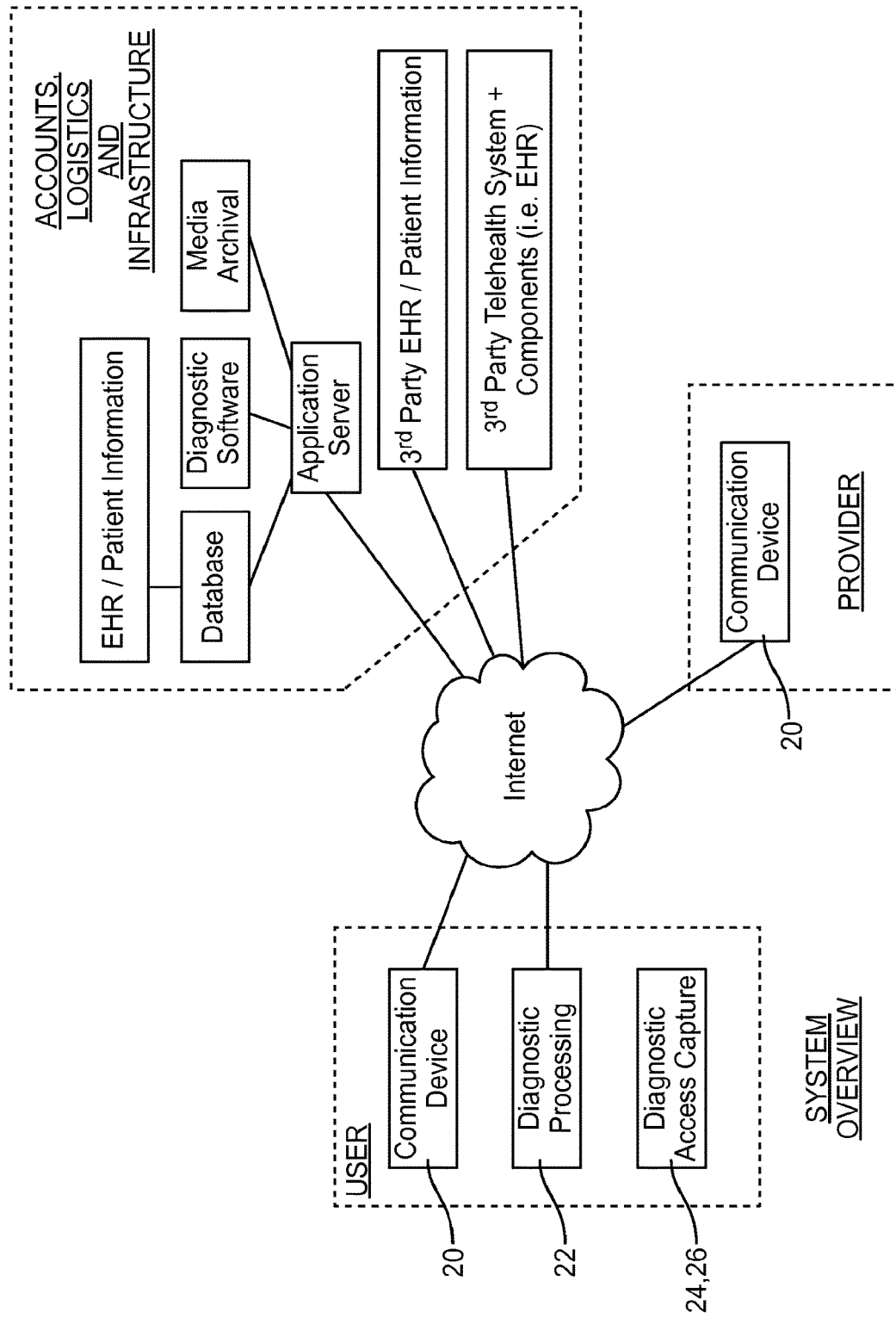
FIG. 3 illustrates linked components of an exemplary embodiment of a telehealth system.

FIG. 3 illustrates linked components of an exemplary embodiment of a telehealth system according to the present invention. The system is comprised of three components: (a) a user subsystem configured for receiving a patient's current medical data; (b) a provider subsystem configured for communicating with a health care provider; and (c) an infrastructure subsystem configured to process and store medical data and diagnostic information received from the user subsystem and the provider subsystem.

In the illustrated embodiment, the user subsystem comprises a communication device; a diagnostic processing device; and a diagnostic capture device. The provider subsystem comprises a communication device. The infrastructure subsystem comprises: (a) an application server comprising computer instruction code configured for communication with (i) a database configured to store a patient's personal information and electronic health record as well as information on providers; (ii) diagnostic computer instruction code configured to receive current patient medical information and to provide diagnostic information concerning the patient's medical condition; and (iii) a database configured to store archived diagnostic information; (b) a server comprising computer instruction code configured to communicate with one or more third-party patient personal information or electronic health record databases; and (c) a server comprising computer instruction code configured to communicate with a third party telehealth system.

Figure 4:
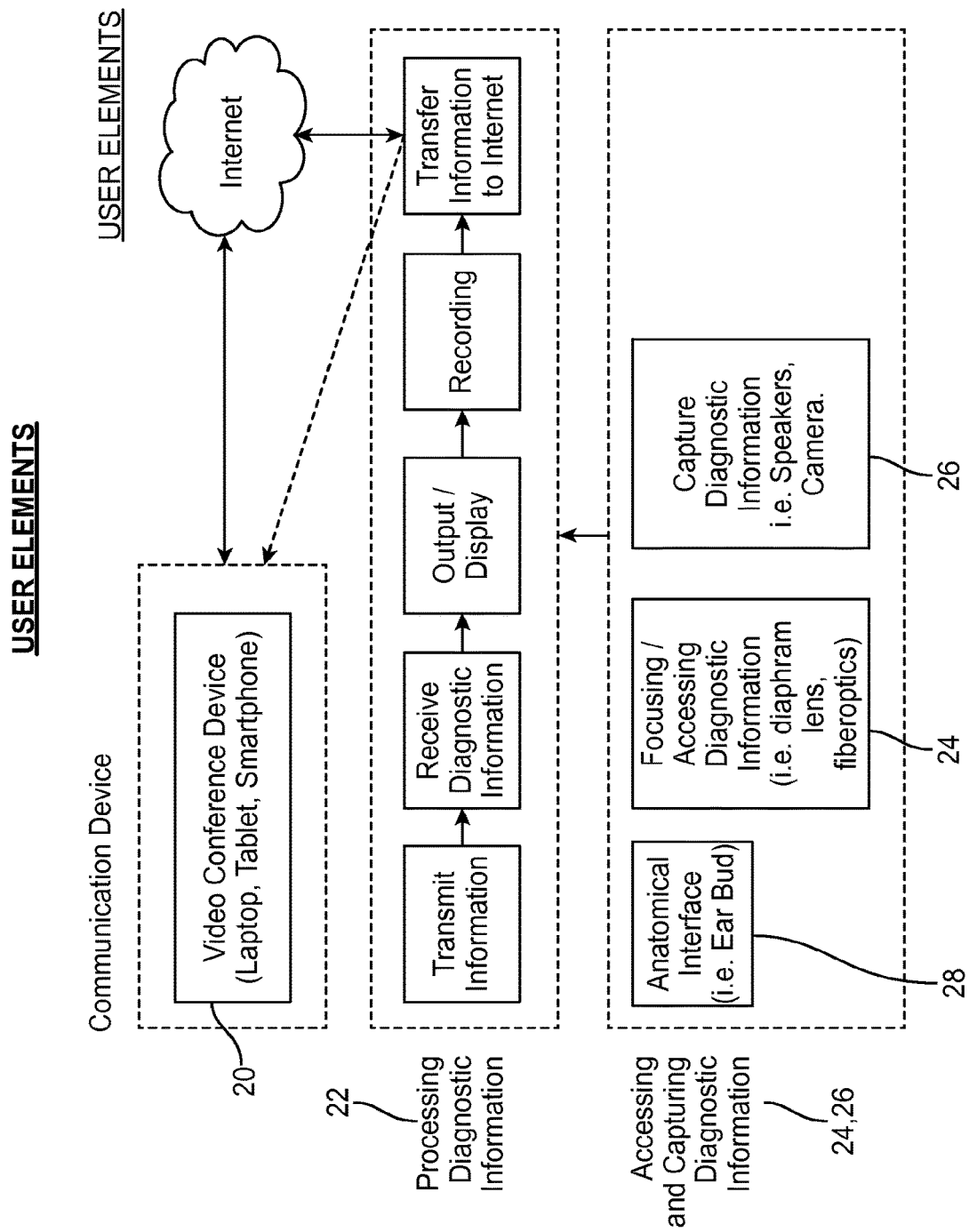
FIG. 4 illustrates three components of a telehealth system in accordance with an exemplary embodiment of the invention.

FIG. 4 illustrates three components of a user subsystem of a telehealth system in accordance with an exemplary embodiment of the invention. The user subsystem comprises a communication device, which can be capable of participating in a video conference. For example, the communication device can be a laptop, tablet, or smartphone equipped with a video camera.

The user subsystem also comprises a module which processed diagnostic information. This system transmits information, receives diagnostic information, outputs or displays information, records any diagnostic data, and transfers this information to the Internet, for example, to a storage unit which may be cloud-based or stored or warehoused on a proprietary site and/or to the communication device.

The user subsystem also comprises a module which accesses and captures diagnostic information. This module can comprise an anatomical interface, such as an earbud, and can focus and access diagnostic information via a diaphragm, lens, fiberoptics, or other element. This module can also capture diagnostic information via speakers or a camera.

Figure 5:
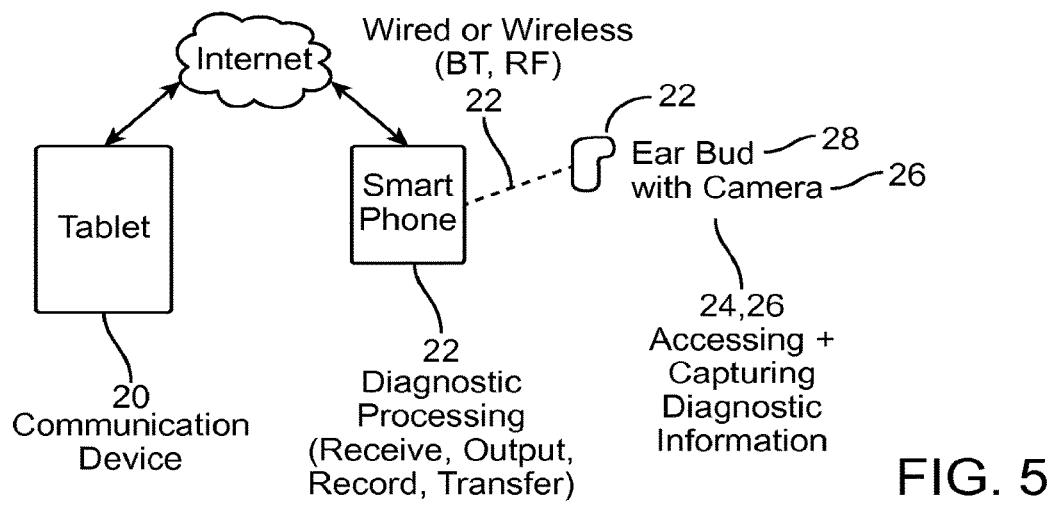
FIGS. 5-7 illustrate exemplary embodiments of user devices structurally configured for insertion into the human ear which communicate a patient's current medical status in accordance with the present invention.
Figure 6:
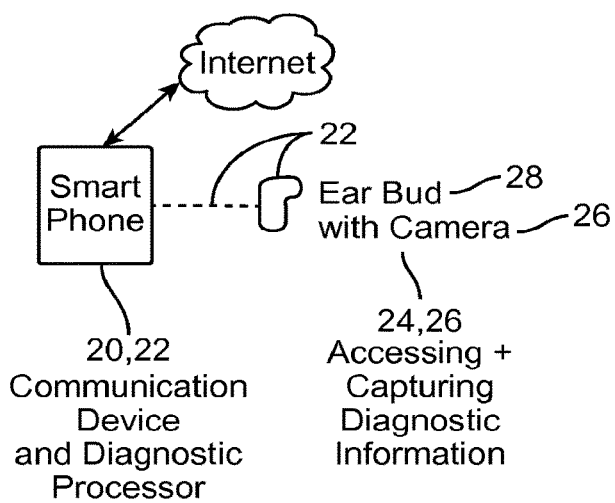
Figure 7:
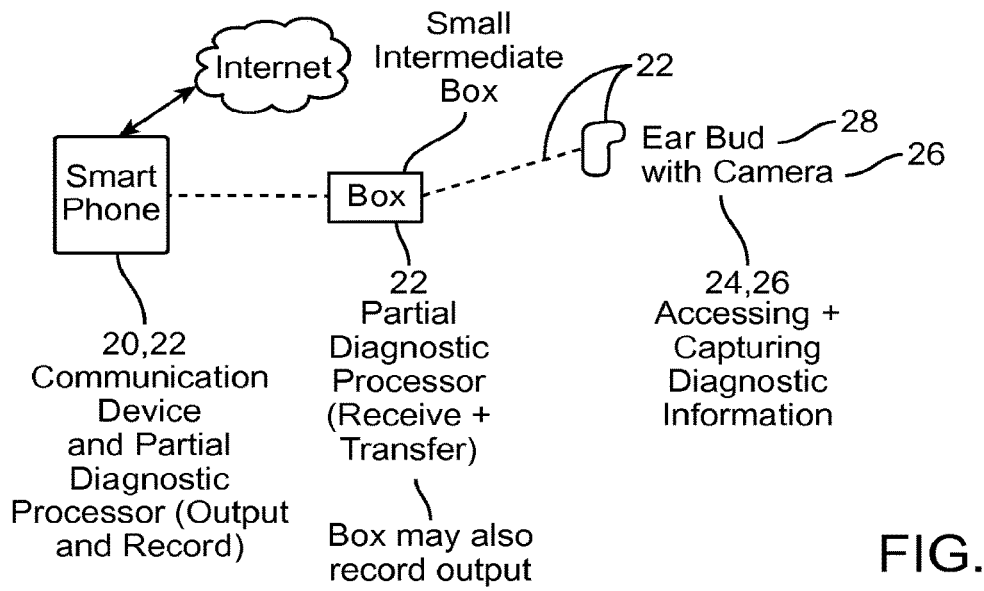

FIGS. 5-7 illustrate exemplary embodiments of user devices structurally configured for insertion into the human ear which communicate a patient's current medical status in accordance with the present invention. The user devices can include various kinds of communications devices, which may not have any diagnostic capabilities (as shown in FIG. 5), or which can have a diagnostic processor (as shown in FIG. 6), or which can have a partial diagnostic processor (as shown in FIG. 7). In these Figures, an ear bud having a camera is used to access and capture diagnostic information, and the ear bud communicates directly with a smartphone (FIGS. 5 and 6), or indirectly through a small intermediate box which has a partial diagnostic processor for receipt and transfer of information (FIG. 7). The earbud transmits photos of the inside of the ear canal wirelessly via BlueTooth (BT) or radio frequency (RF), although in certain embodiments this information can be transmitted via a wire connected to the jack or port of the tablet, smartphone, or other device.

Figure 8:
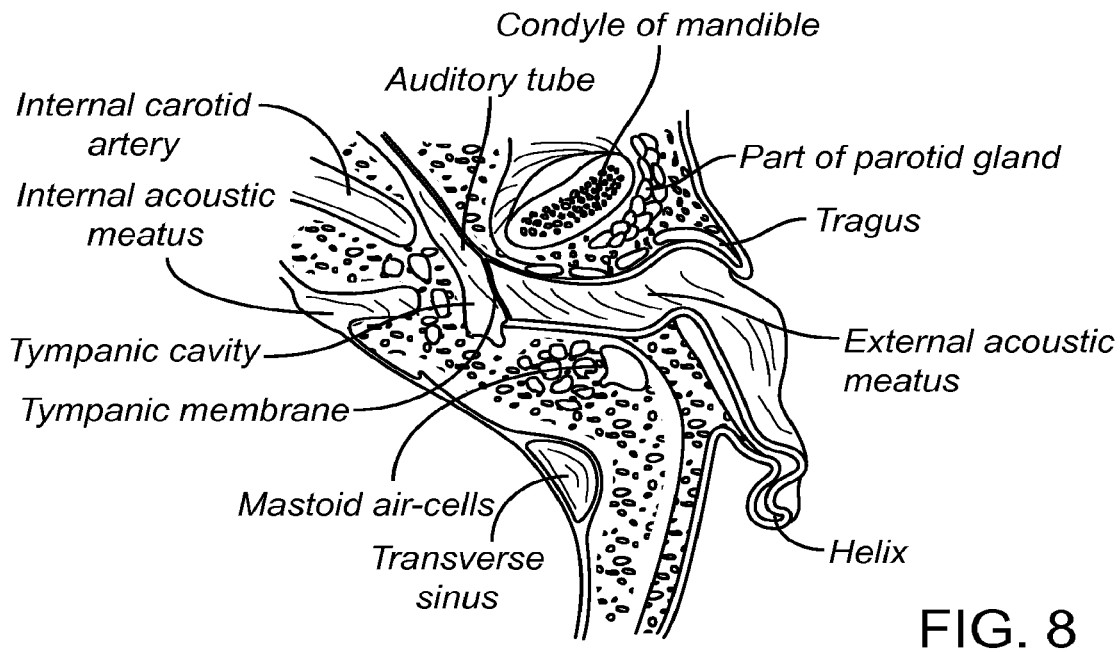
FIGS. 8 and 9 show a cross-section of the ear region of a patient's head for purposes of reference.
Figure 9:
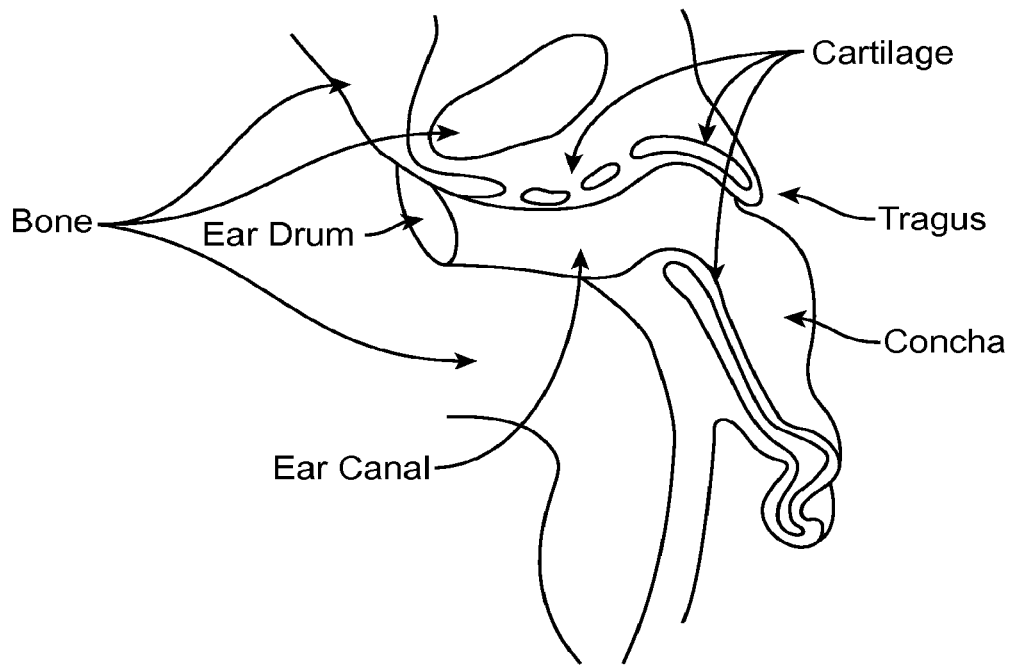

FIGS. 8 and 9 show a cross-section of the ear region of a patient's head for purposes of reference.

FIGS. 10-20 illustrate exemplary embodiments of an ear imaging device comprising an anatomical interface to facilitate positioning and image quality and may also serve as safety mechanisms that prevent over insertion. As discussed earlier, diagnostic devices may contain any combination of elements described. For example, in FIGS. 10-20, outer ear elements may contain LEDs in the outer ear elements which emit light which is transmitted by standard components such as fibers, channels or light pipes.

Figure 10:
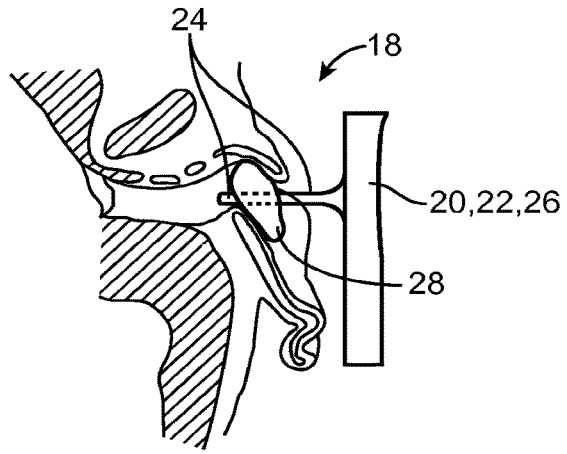
FIGS. 10-20 illustrate exemplary embodiments of an ear imaging device comprising an anatomical interface to facilitate positioning and image quality and may also serve as safety mechanisms that prevent over insertion.

FIG. 10 shows an ear bud which is used to position and align, in the posterior of the ear canal, an imaging apparatus with the ear drum to optimize the quality of the resultant images. The ear bud and imaging apparatus are attached to a port on the smartphone which aligns with the camera for image capturing.

Figure 11:
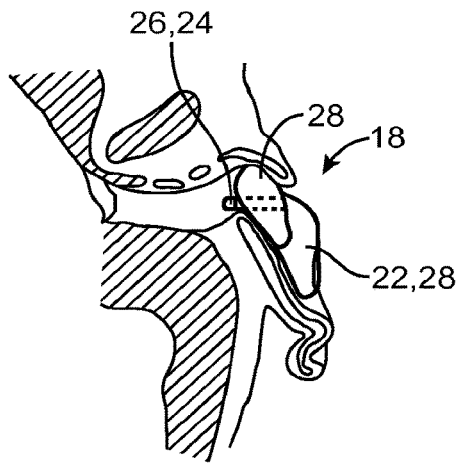

FIG. 11 illustrates an ear bud attached to an outer ear element. The ear bud contains the imaging apparatus with a video chip at its tip. The outer ear element contains the necessary electronics and transfers the image, via radio frequency, BlueTooth, wire, or other protocol, to another device such as a smartphone for output and display of the medical data to the Internet.

Figure 12:
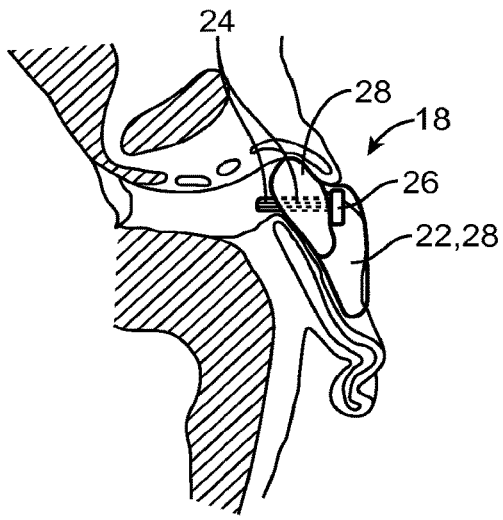

FIG. 12 illustrates an ear bud and outer ear element. In this Figure, the outer ear element contains the video chip as well as any ancillary electronics. The ear bud has fiber optics or a channel to allow transmission of the image to the video chip. The entire embodiment consists of a single hardware element.

Figure 13:
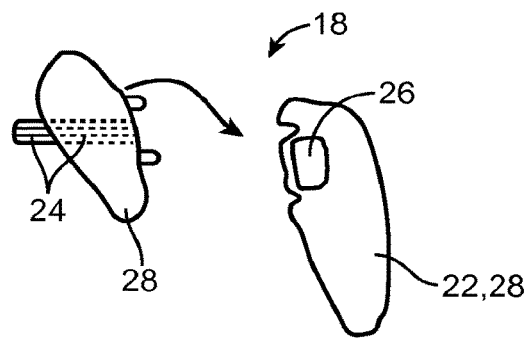

FIG. 13 illustrates another combination of an ear bud and a detachable outer ear element. In contrast to FIG. 12 which shows a single hardware element, FIG. 13 illustrates that the components are detachable. This embodiment allow for different sizes of ear buds to be supplied, as well as permitting different buds for left and right ears when necessary.

Figure 14:
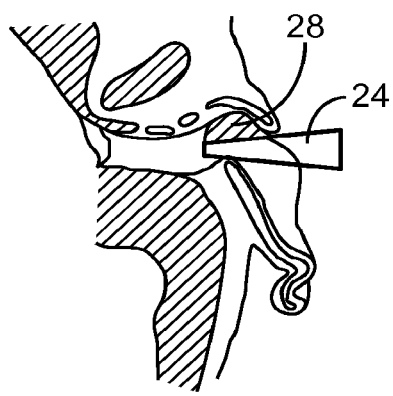

FIG. 14 shows an embodiment of the inventive device in the form of a standard speculum. This embodiment is configured with extra material on the anterior (front) side in order to position the speculum to a more posterior (backward) position for better alignment with the ear drum.

Figure 15:
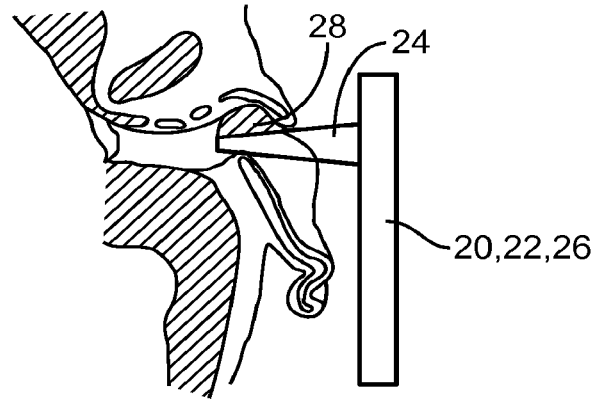

FIG. 15 illustrates an embodiment of the inventive device in the form of a speculum, with an anterior buildup and extension attached to a smartphone for image capture. The speculum element may alternatively be attached to a different diagnostic processing device (such as the outer ear element shown in the earlier Figures) to capture the image.

Figure 16:
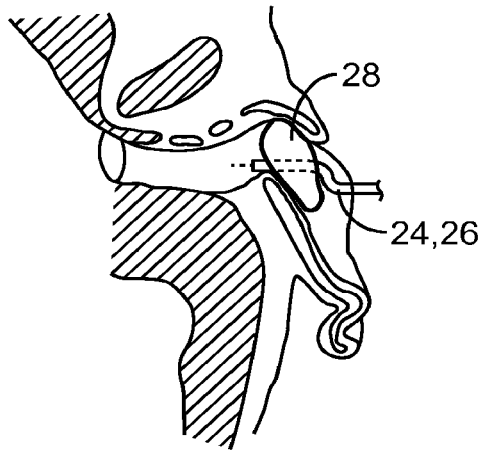
Figure 17:
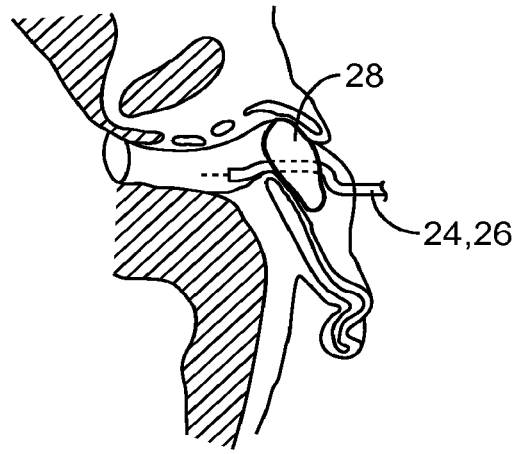
Figure 18:
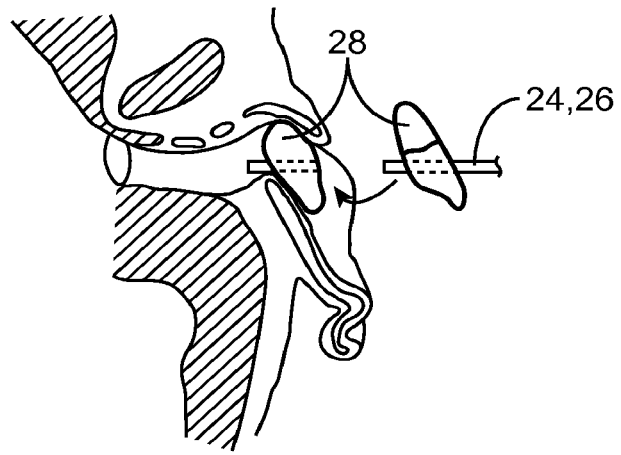
Figure 19:
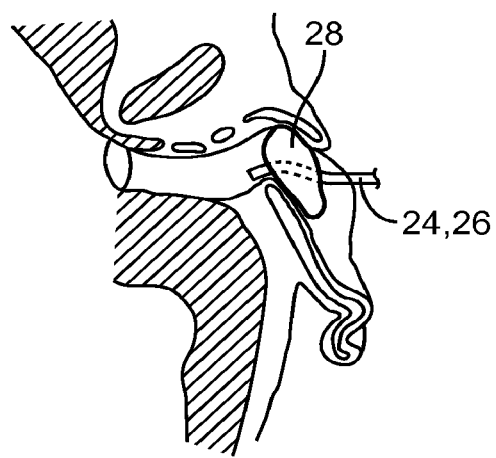
Figure 20:
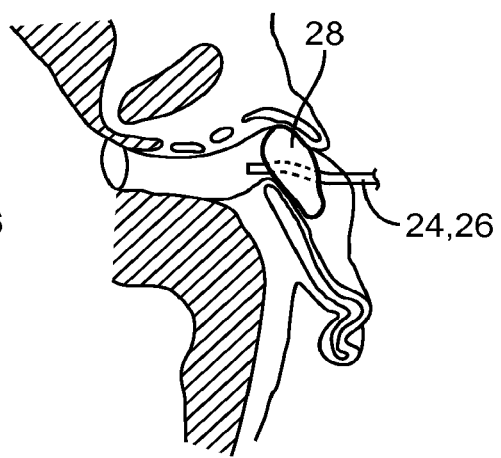

FIGS. 16-18 show alternative examples of ear buds and imaging apparatus. FIG. 18 shows a compressible ear bud with an imaging apparatus for conformity and secure fitting with an individual's ear. FIGS. 19 and 20 show examples of an ear bud and imaging apparatus that repositions itself as the ear is manipulated.

Figure 21:
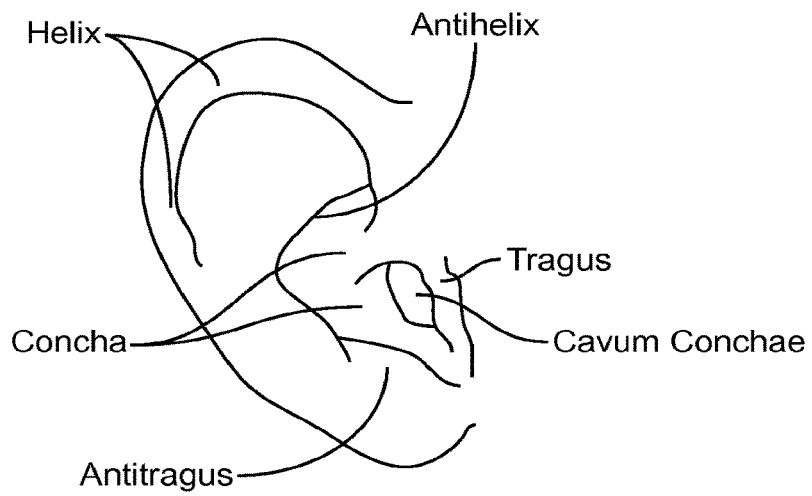
FIG. 21 illustrates features of the outer human ear for purposes of reference.

FIG. 21 illustrates features of the outer human ear for purposes of reference.

Figure 22:
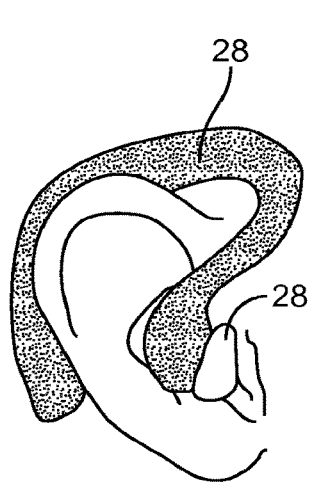
FIGS. 22-24 illustrate exemplary embodiments of an over-ear device for obtaining a patient's current medical status.
Figure 23:
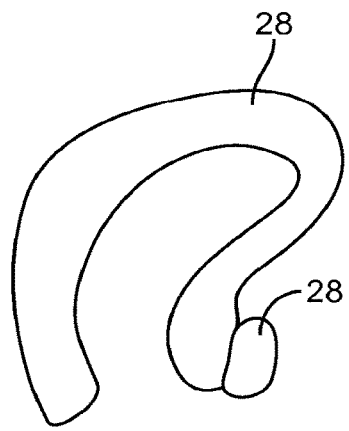
Figure 24:
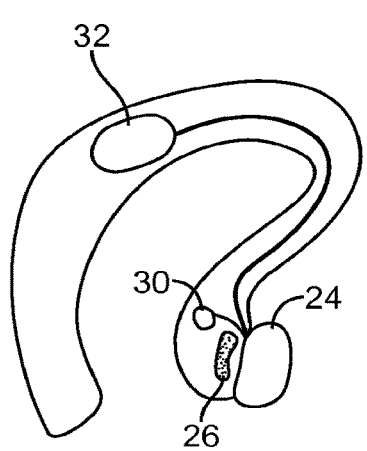

FIGS. 22-24 illustrate exemplary embodiments of an over-ear device for obtaining a patient's current medical status. FIG. 22 shows an over ear device, comprised of an outer ear element on the helix, and an ear bud inside the ear canal. FIG. 23 shows the embodiment of FIG. 22 separately from the ear for clarity of view. FIG. 24 shows an embodiment of an over ear device to which a video chip, a light source, and a speaker have been affixed.

Figure 25:
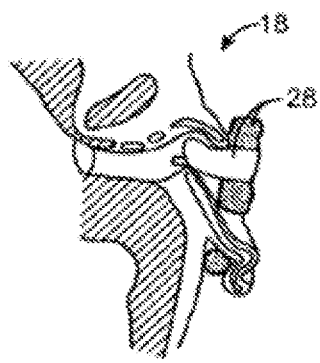
FIGS. 25 and 26A-D illustrate exemplary embodiments of an over-ear device and different configuration of the outer ear elements.
Figure 26A:
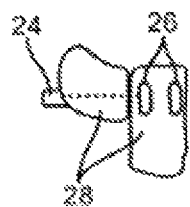
Figure 26B:
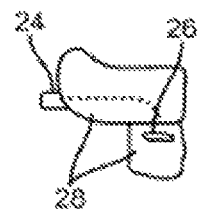
Figure 26C:
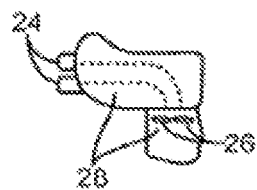
Figure 26D:
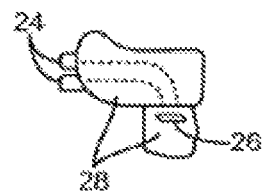

FIGS. 25-26A-D illustrate exemplary embodiments of an over-ear device and different configurations of the outer ear elements. FIG. 25 shows a bottom view of an over ear device. A video chip is illustrated within the outer ear element (the over ear piece). FIGS. 26A-D show a plurality of different configurations of outer ear elements, ear buds, and video chips. An outer ear element may be configured with one or more video chips to allow for left and right ear buds to be attached. More than one image may also be captured, for example, at different locations of the ear, or at different angles.

Figure 27:
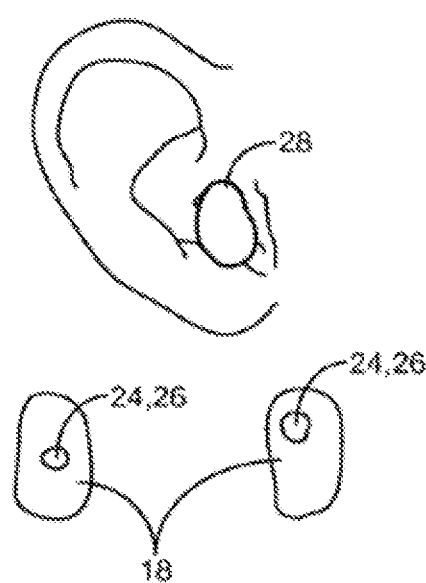
FIGS. 27 and 28A-F illustrate side and bottom views of an exemplary ear imaging device.
Figure 28A:
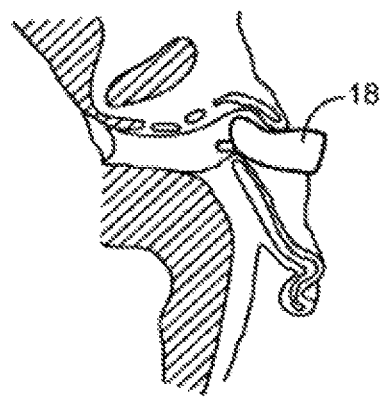
Figure 28B:
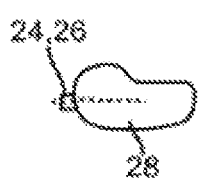
Figure 28C:
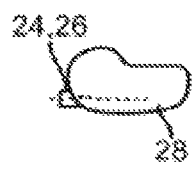
Figure 28D:
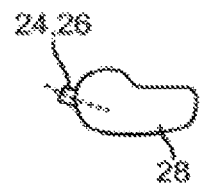
Figure 28E:
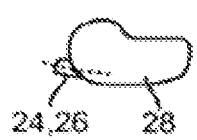
Figure 28F:

FIGS. 27 and 28A-F illustrate side and bottom views of an exemplary ear imaging device. FIG. 27 shows a side view of an ear imaging device. The device may be configured for interface with the subject's anatomy so that the images are captured centrally or off-center, as shown in the lower two illustrations. FIGS. 28A-F show bottom views of an ear imaging device. The device may be configured and interfaced with the subject's anatomy so that images are captured centrally, off-center, and/or at an angle, as illustrated in the five drawings at the bottom of the Figure.

Figure 29:
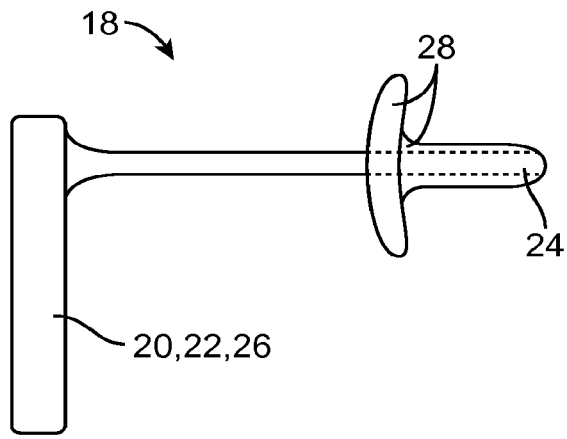
FIGS. 29 and 30 illustrate exemplary embodiments of anatomical interfaces for an medical device for insertion into a patient's mouth or ear.
Figure 30:
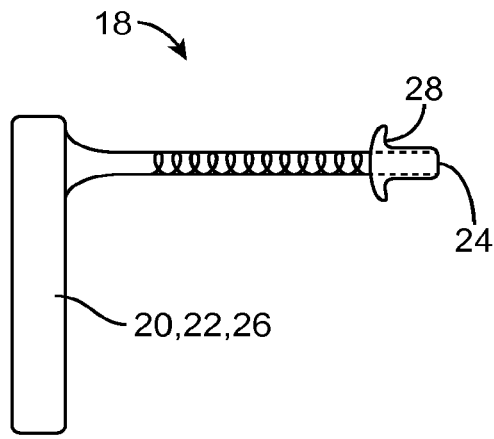

FIGS. 29 and 30 illustrate exemplary embodiments of anatomical interfaces for a medical device for insertion into a patient's mouth (FIG. 29) or ear (FIG. 30). The anatomical interfaces are attached to a smartphone in the illustrated embodiment. The attachment of the anatomical interface to the device may be rigid (FIG. 29), or flexible as shown in FIG. 30 with a spring/coil combination.

Figure 31:
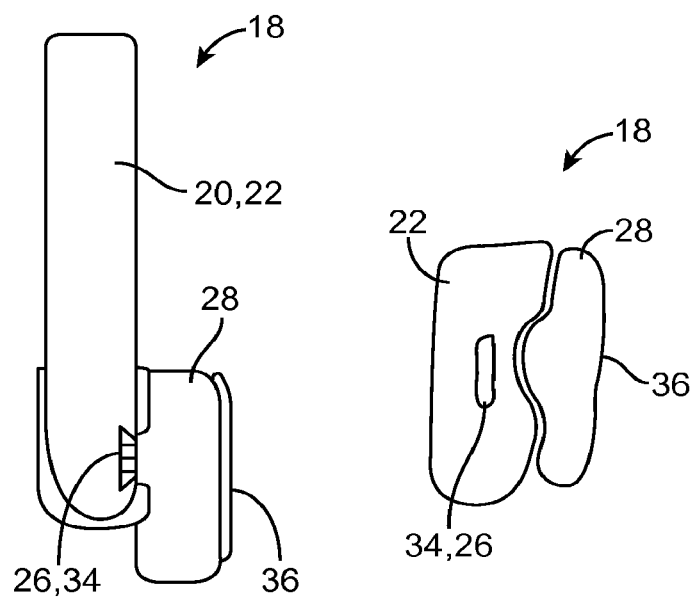
FIG. 31 illustrates an exemplary embodiment of a medical diagnostic instrument equipped with a microphone.

FIG. 31 illustrates an exemplary embodiment of a medical diagnostic instrument equipped with a microphone. In the first image, a diaphragm, anatomical interface, and accessing device are shown attached to a smartphone with a microphone for capturing sound. In the second image, a diaphragm, anatomical interface, and accessing device are attached to a specialty diagnostic capturing unit with a microphone which transmits sounds via a wired or wireless connection. Such an embodiment can be used to listen to heart or lung sounds, and the device can be used to perform the functions of a standard stethoscope.

FIGS. 32-35 illustrate exemplary embodiments of medical diagnostic instruments for collection of patient medical information. FIG. 32 shows a strap with microphones. This embodiment can be used, for example, to listen to a patient's chest or lungs when applied to a patient's chest. Similarly, FIG. 33 shows a shirt or vest which contains microphones. When the patient dons such articles as the strap or shirt/vest, the health care provider can listen remotely to sounds from the patient's body and thereby provide a diagnosis of a medical condition.

FIG. 34 illustrates an oral device, in the general form of a pacifier, which contains a lens and video chip for use in examining a patient's mouth or oral cavity. The oral device is equipped with digital imaging elements which communicate with a diagnostic processor to enable remote diagnoses. Such embodiments are useful to any patient, although they will provide particular application to small children.

FIG. 35 shows an embodiment of a medical device comprising an oral device and an ear bud. The oral device and the ear buds both have fiber optics or channel to interface with a device having a video chip and the associated ancillary electronics, and these elements communicate with a diagnostic processor to provide medical data of at least two separate parts of patient's body.

Figure 36:
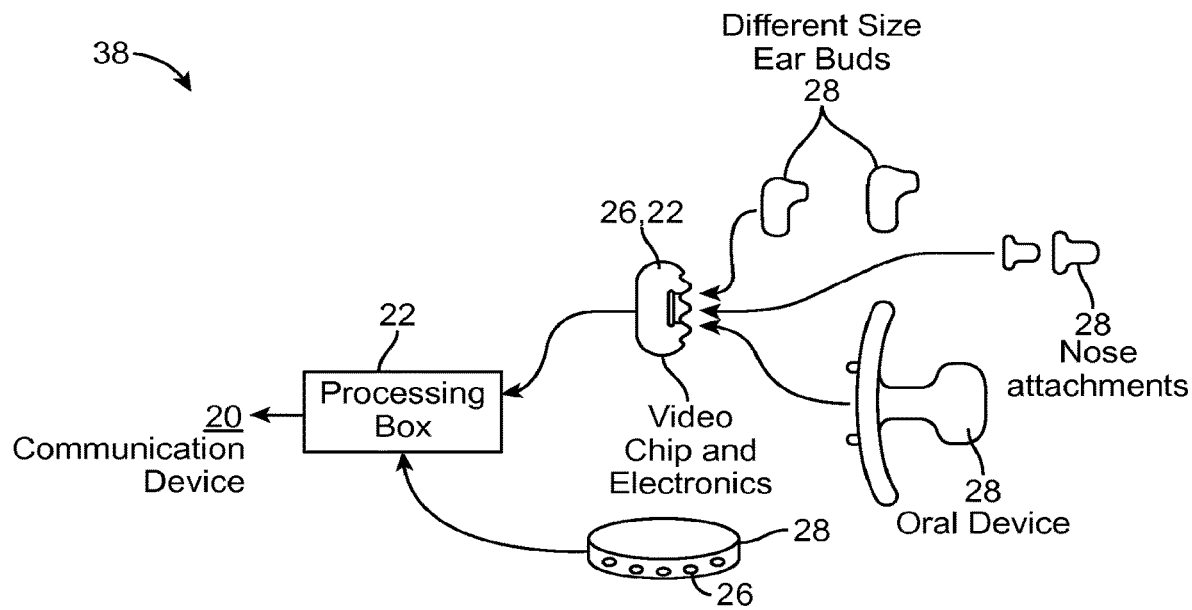
FIGS. 36-37 illustrate exemplary embodiments of kits comprising devices for accessing, capturing, and at least partial processing of medical diagnostic information in accordance with the present invention.
Figure 37:
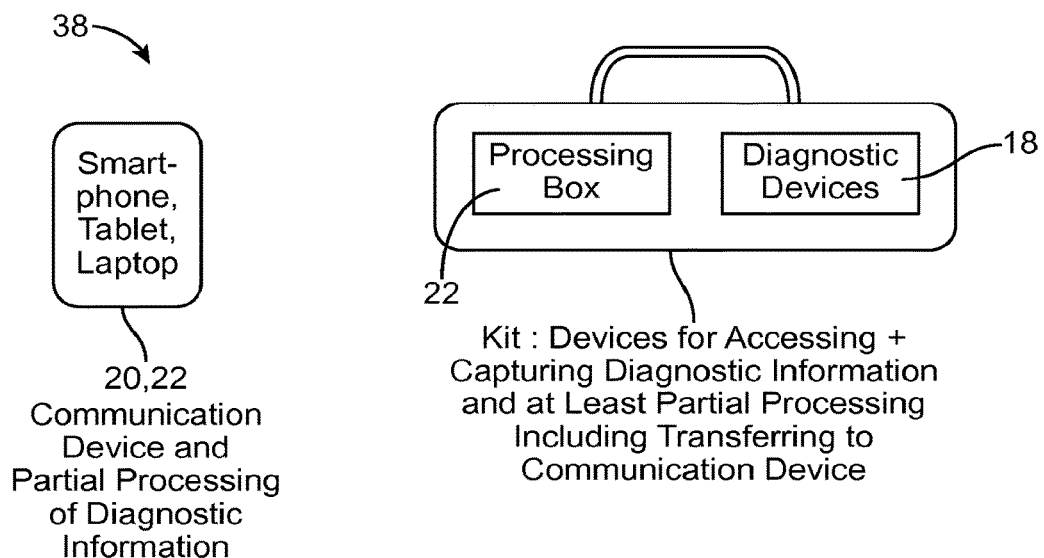

FIGS. 36-37 illustrate exemplary embodiments of kits comprising devices for accessing, capturing, and at least partial processing of medical diagnostic information in accordance with the present invention. FIG. 36 shows a kit comprising a strap equipped with microphones, an oral device, nose attachments, and different sized ear buds. These elements all communicate with a processing box which interfaces with a communication device for transmission of data to the medical provider. Any combination of these elements can be used in accordance with the present invention to transmit patient medical data to a provider. FIG. 37 shows a kit comprising a computing device, such as a smartphone, tablet, or laptop, to provide communication and partial processing of diagnostic information. The kit also comprises devices for accessing and capturing diagnostic information and at least partial processing of the medical data, including transferring the information to a communication device such as the smartphone, tablet, or laptop just described.

FIGS. 38A-38E illustrate exemplary embodiments of medical diagnostic devices in accordance with the present invention which are structurally configured to be placed on, in, or adjacent to a patient's body for obtaining medical diagnostic information. These devices can contain a battery in an inner compartment for powering the device or for transmission of obtained medical data.

Figure 38A:
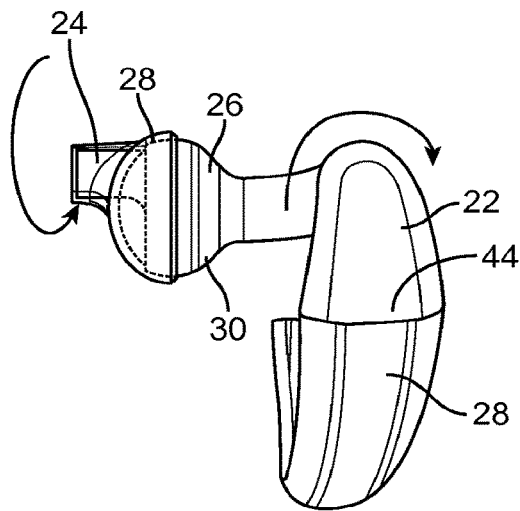
FIGS. 38A-38E illustrate exemplary embodiments of medical diagnostic devices in accordance with the present invention which are structurally configured to be placed on, in, or adjacent to a patient's body for obtaining medical diagnostic information.
Figure 38B:
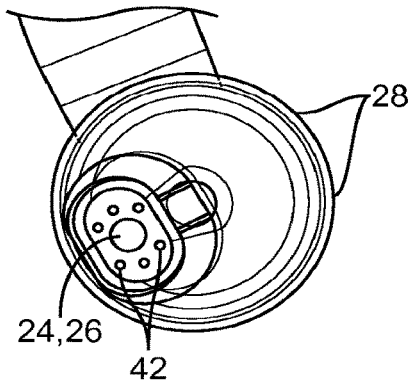

FIGS. 38A-38B illustrate exemplary embodiments of medical diagnostic devices having an anatomical interface, and which are structurally configured to be placed into a patient's ear canal. The illustrated devices are rotatable about certain positions to permit optimal fitting into the ear canal.

Figure 38C:
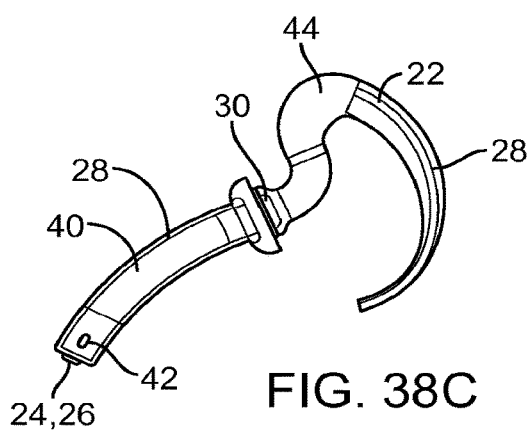
Figure 38D:
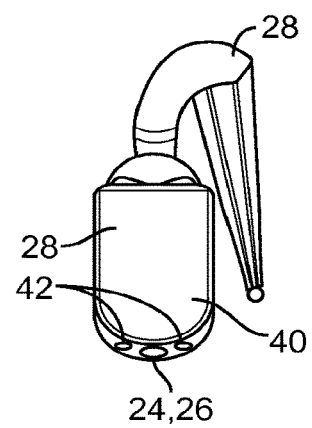

FIGS. 38C-38D illustrate exemplary embodiments of medical diagnostic devices which are structurally configured to be placed in a patient's oral cavity. The devices have a main body which can be inserted into the patient's oral cavity to permit optimal data collection. These medical diagnostic devices have an anatomical interface component which interfaces with the user's hand.

Figure 38E:
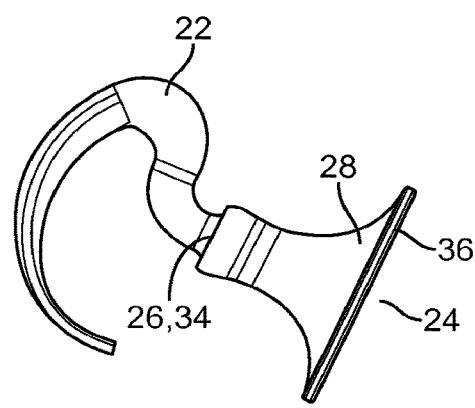

FIG. 38E illustrates an exemplary embodiment of a medical diagnostic device which has stethoscope capabilities, and which is structurally configured for listening to sounds from a patient's body. The device has an anatomical interface component which can be applied to a patient's chest, back, joint, or other location for listening to sounds.

The various embodiments described above can be combined to provide further embodiments. Aspects of the embodiments can be modified, if necessary to employ concepts of the various patents, application and publications to provide yet further embodiments.

Other objects, advantages and embodiments of the various aspects of the present invention will be apparent to those who are skilled in the field of the invention and are within the scope of the description and the accompanying figure. For example, but without limitation, structural or functional elements might be rearranged, or method steps reordered, consistent with the present invention. Similarly, a device may comprise a single instance of a device or comprise a plurality of devices, such plurality functioning as a single device working in tandem. For example, a computing device may consist of a plurality of computing devices which together provide the desired functionality. The device types described in various embodiments are not meant to limit the possible types of devices that may be used in embodiments of aspects of the present invention, and other types of devices that may accomplish similar tasks may be implemented as well. Similarly, principles according to the present invention, and methods and systems that embody them, could be applied to other examples, which, even if not specifically described here in detail, would nevertheless be within the scope of the present invention.

The following listing identifies elements illustrated in the Figures and provides the respective figure reference numeral for each of the identified elements.

| Reference Numeral | Element |
|---|---|
| 10 | Telehealth system |
| 12 | Provider |
| 14 | Caregiver |
| 16 | Patient |
| 18 | Diagnostic device |
| 20 | Communication component |
| 22 | Processing component |
| 24 | Accessing element |
| 26 | Capturing element |
| 28 | Anatomical interface component |
| 30 | Light source |
| 32 | Speaker |
| 34 | Microphone |
| 36 | Diaphram |
| 38 | Kit |
| 40 | Oral device |
| 42 | Light emitting |
| 44 | Battery |

What is claimed is:

1. An imaging apparatus for obtaining images inside a patient's ear canal, the imaging apparatus comprising:
   a main body;
   an insertion portion connected to the main body, the insertion portion adapted for insertion into the ear canal while the main body remains external to the ear canal, the insertion portion including:
      a speaker;
      a first extension connected to the main body, the first extension having a shape configured to fit into the ear canal;

a second extension that extends from the first extension, a central axis of the second extension offset from a central axis of the first extension by a non-zero distance at a location where the second extension extends from the first extension, the second extension extending further into the ear canal than the first extension; and an imaging element housed within the second extension, the imaging element configured for obtaining an image of the ear canal and/or an ear drum.

2. The imaging apparatus according to claim 1, wherein the imaging apparatus comprises a wireless transmission element for wirelessly transmitting the obtained images to a computing device.

3. The imaging apparatus according to claim 1, wherein at least one of the first extension or the second extension has a soft outer surface for improved patient comfort during insertion of the first extension or the second extension into the patient's ear canal.

4. The imaging apparatus according to claim 1, wherein the second extension is removable from the main body, and wherein the imaging apparatus further comprises:

a third extension configured to be coupled to the main body, the third extension structurally configured for insertion into the patient's oral cavity; and an additional imaging element, housed within the third extension, structurally configured for obtaining images of the patient's oral cavity.

5. The imaging apparatus according to claim 1, wherein the second extension is removable from the main body, and wherein the imaging apparatus further comprises:

a third extension configured to be coupled to the main body; and a sound accessing element, housed within the third extension, structurally configured for obtaining sounds from the patient's body.

6. The imaging apparatus of claim 1, wherein the central axis of the second extension is angled at a non-zero angle from the central axis of the first extension.

7. The imaging apparatus according to claim 6, wherein the central axis of the second extension is angled at the non-zero angle from the central axis of the first extension at the location where the second extension extends from the first extension.

8. The imaging apparatus according to claim 1, wherein a length of insertion of the second extension into the ear canal is changeable.

9. The imaging apparatus according to claim 8, wherein the length of insertion of the second extension is changeable using a screw-type adjustment.

10. The imaging apparatus according to claim 8, wherein the insertion portion further comprises a balloon adapted to act as a stop.

11. The imaging apparatus according to claim 1, wherein a center of a lens of the imaging element is offset from a central axis of the second extension at a tip of the second extension.

* * * * *

UNITED STATES PATENT AND TRADEMARK OFFICE
CERTIFICATE OF CORRECTION

PATENT NO. : 11,011,271 B2
APPLICATION NO. : 15/920208
DATED : May 18, 2021
INVENTOR(S) : Boucher et al.

Page 1 of 1

It is certified that error appears in the above-identified patent and that said Letters Patent is hereby corrected as shown below:

In the Claims

In Column 34, in Claim 1, Line 59, after "body;" insert -- and --.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*